United States Patent
Huge et al.

(10) Patent No.: US 6,783,361 B2
(45) Date of Patent: Aug. 31, 2004

(54) ORTHODONTIC MECHANICAL FORCE MODULE

(75) Inventors: Scott A. Huge, Cumming, GA (US); Arlen J. Hurt, Dacula, GA (US); Steven A. Franseen, Lakewood, CO (US)

(73) Assignee: Specialty Appliances Works, Inc., Cumming, GA (US)

( * ) Notice: Subject to any disclaimer, the term of this patent is extended or adjusted under 35 U.S.C. 154(b) by 0 days.

(21) Appl. No.: 10/262,248

(22) Filed: Oct. 1, 2002

(65) Prior Publication Data

US 2003/0207225 A1 Nov. 6, 2003

Related U.S. Application Data

(60) Provisional application No. 60/358,763, filed on Feb. 22, 2002.

(51) Int. Cl.[7] .................................................. A61C 3/00
(52) U.S. Cl. .......................................................... 433/7
(58) Field of Search .................................... 433/7, 5, 18

(56) References Cited

U.S. PATENT DOCUMENTS

| | | | |
|---|---|---|---|
| 618,105 A | 1/1899 | Knapp | 433/7 |
| 1,773,588 A | * 8/1930 | Linde | 433/7 |
| 4,090,299 A | 5/1978 | Williams | 433/18 |
| 4,379,693 A | 4/1983 | Wallshein | 433/7 |
| 5,133,659 A | 7/1992 | Shilliday | 433/3 |
| 5,238,402 A | 8/1993 | Rohlcke et al. | 433/2 |
| 5,281,133 A | 1/1994 | Farzin-Nia | 433/7 |
| 5,292,249 A | 3/1994 | German | 433/22 |
| 5,326,259 A | 7/1994 | Rohlcke et al. | 433/8 |
| 5,439,377 A | 8/1995 | Milanovich | 433/7 |
| 5,975,894 A | 11/1999 | Pozzi | 433/7 |
| 6,241,517 B1 | 6/2001 | Williams | 433/19 |
| 6,267,589 B1 | 7/2001 | Farzin-Nia et al. | 433/7 |

* cited by examiner

Primary Examiner—John J Wilson
(74) Attorney, Agent, or Firm—Marsh Fischmann & Breyfogle LLP

(57) ABSTRACT

The present invention is generally directed to an orthodontic mechanical force module having a jack screw whose rotation is controlled by a ratchet. In one embodiment, a pair of housings are interconnected with the patient in any appropriate manner, and are further rotatably interconnected with a rotatable spindle. At least one of these housings is also threadably engaged with the spindle. A ratchet is associated with the spindle to selectively allow the spindle to rotate only in a direction that increases a magnitude of the treatment forces being exerted on the patient by changing the spacing between the pair of housings by a movement of at least one of the housings along the spindle due to its rotation. That is, in an active position the ratchet precludes the spindle from rotating in a direction that would tend to reduce the magnitude of the treatment forces being exerted on the patient.

54 Claims, 10 Drawing Sheets

ORTHODONTIC MECHANICAL FORCE MODULE

RELATED APPLICATIONS

This application claims priority from U.S. Provisional Patent Application Serial No. 60/358,763, filed Feb. 22, 2002, entitled "Ratcheting Expansion Screw", the entire disclosure of which is incorporated by reference in its entirety herein.

FIELD OF THE INVENTION

The present invention generally relates to orthodontics and, more particularly, to an orthodontic appliance that exerts a desired force on a patient to change at least one spacing associated with the patient (e.g., palatal expansion).

BACKGROUND OF THE INVENTION

It is oftentimes necessary to expand the palate as an orthopedic prerequisite for orthodontic treatment. Palatal expansion increases arch length as needed to correct crowding and in the process, establishes a more morphologic arch form for subsequently establishing the aesthetic orthodontic alignment of the teeth. Narrow, constricted arches are often the result of destructive oral habits such as thumb sucking and tongue thrusting. The sequela of such habits not only makes attainment and maintenance of a stable transverse width difficult, such conditions are commonly associated with significant orthodontic mal-alignment of the teeth as well as a non-harmonious occlusion between the arches. For many orthodontic cases, the orthopedic step of palatal expansion must be accomplished before the subsequent steps of orthodontically moving the teeth into alignment and orthopedically moving both arches into a harmonious relationship.

Palatal expansion of the above-noted type is commonly accomplished utilizing a palatal expansion device known as an expansion screw. The method of palatal expansion using expansion screws has become known in the art as "rapid palatal expansion" (RPE). Conventional palatal expansion devices are at least generally rigid structures that typically include at least one screw mechanism (e.g., a jackscrew). Such conventional palatal expansion devices may be installed into an oral cavity of a patient in a variety of appropriate manners, such as by interconnecting the device to one or more teeth on each side of the palatal suture or a sagittal midline of the arch. Typically, torquing/rotating the screw mechanism of the palatal expansion device to a desired position at least assists in generating expansive force on the patient's palate. Over time, exertion of this expansive force on the patient's palate due to utilizing such a palatal expansion device ideally results in a widening of the patient's palate.

The above-described type of palatal expansion device is most commonly installed on the upper dental arch of a patient by an appropriate professional (e.g., an orthodontist). Subsequent to installation of the device, regular and/or systematic adjustment of the device is generally desired to promote the potential for appropriate change in spacing of the patient's dental arch. This adjustment is typically attempted via an individual (e.g., the patient, a relative or friend of the patient or otherwise) reaching into and/or inserting a tool into the patient's oral cavity and thereafter rotating/torquing the above-mentioned screw mechanism of the palatal expansion device. For example, an orthodontist may prescribe that the patient have the patient's mother or father adjust the palatal expansion device every evening via rotating the screw mechanism a defined amount. However, adjustment of these palatal expansion devices has left much to be desired in that the individual generally responsible for making these adjustments typically does not have in education in orthodontics or orthodontic devices, and thus, typically has not been equipped with a way of providing that such adjustments exhibit the prescribed amount of rotational adjustment on a day-to-day basis. Accordingly, this may result in inefficient treatment due to these regular adjustments falling short of the prescribed amount of screw rotation. Alternatively, this may result in an increased potential for unnecessary pain and/or injury to the patient as a result of one or more of the adjustments exceeding the prescribed amount of rotation.

In addition, rather significant treatment forces may be exerted on the patient by utilizing these types of palatal expansion devices. As mentioned above, the expansive force of a particular expansion device is typically altered by rotating/torquing the associated screw mechanism (e.g., jackscrew). This expansive force is at least generally physiologically/anatomically resisted by reciprocal (i.e., contractile or compression) forces due to the patient's biological makeup, which promote a "status quo" contour/shape of the palate. In other words, these reciprocal forces tend to oppose augmentation of the arch of the oral cavity. Moreover, these reciprocal forces may potentially exact enough force on the palatal expansion device that the screw mechanism may undesirably back out or unwind with regard to the rest of the palatal expansion device. This is commonly referred to as "backoff." "Back-off" also occurs due to the reciprocal, resistive physiological forces, in combination with slight flexing of an appliance structure during mastication, speaking and normal tongue movement. Such movements or slight flexing of the appliance, during use, all contribute to "walking" of the screw in the direction of least resistance, which is "back-off." In any case, the design/configuration of the screw mechanisms of these palatal expansion devices typically enables these devices to "loosen" or contract and provide less than the desired amount of expansive force on the patient's palate.

Accordingly, it would be desirable to provide a palatal expansion device that increases the potential for adjusting the palatal expansion device in a substantially controlled/defined manner. Similarly, it would be desirable to provide a palatal expansion device that increases the potential for promoting/maintaining desired levels of expansive forces upon installation into the oral cavity of a patient.

SUMMARY OF THE INVENTION

Accordingly, the present invention is generally embodied by an orthodontic mechanical force module that may be designed to selectively enable only unidirectional adjustment (e.g., rotation) of an associated screw mechanism (or "spindle") to increase the treatment forces, and thereby decreasing the potential of an undesired reduction of these treatment forces over time. Moreover, the design of such an orthodontic mechanical force module of the present invention may desirably promote one or both of achieving and maintaining a desired positioning of the screw mechanism (or "spindle") relative to the remainder of the orthodontic mechanical force module by enabling regular, predetermined incremental advances for the screw mechanism. Although the present invention is particularly suited for use in palatal expansion applications, the present invention may be applicable to any type of orthodontic treatment where a change in a spacing is a desirable objective (e.g., for distalizing molars on one side of a given dental arch), and regardless of whether this change in spacing is an increase or a decrease.

Adjustment of the treatment forces associated with one or more aspects of the present invention may occur on a relatively frequent basis due to the significant biological response elicited in typically young and growing adolescent patients. In many cases, daily adjustment of the treatment forces associated with one or more aspects of the present invention will be prescribed by an orthodontist. As such, the benefits associated with the one or more aspects of the present invention in reducing the potential for an undesired reduction of treatment forces will be similarly utilized on an equally frequent basis.

A first aspect of the present invention is embodied by an orthodontic mechanical force module that includes first and second housings. A rotatable spindle is rotatably interconnected with both the first and second housings. The spindle is further threadably interconnected with the first housing. That is, both the first housing and at least a portion of the spindle are threaded. Rotation of the spindle thereby causes the first housing to move along the spindle (e.g., along its length dimension) while the spindle rotates relative to both the first and second housings. A ratchet is associated with the spindle and is of the type that when engaged or active, allows for rotation of the spindle in one direction, but not in the opposite direction.

Various refinements exist of the features noted in relation to the subject first aspect of the present invention. Further features may also be incorporated in the subject first aspect of the present invention as well. These refinements and additional features may exist individually or in any combination. The first and second housings may be interconnected with a patient in any appropriate manner. For instance, the first and second housing may each be directly attached to the buccal of a tooth on one side of a patient's dental arch for a molar distalization application or otherwise. In a palatal expansion application, the first housing may be interconnected in any appropriate manner with one side of the patient's dental arch, while the second housing may be interconnected in any appropriate manner with the opposite side of the patient's dental arch. For example, one portion of a separate suitable wire may be fixed or anchored (e.g., soldered; brazed; welded) to each of the first and second housings, while another portion of this same wire may be fixed or anchored (e.g., soldered; brazed; welded) to a band disposed on the patient's tooth and/or structure interconnected therewith (e.g., a lingual wire segment that is fixed to the band and that engages multiple teeth on lingual side thereof). Multiple wires could be attached to each of the first and second housings as well.

The second housing associated with the orthodontic mechanical force module of the first aspect may remain at the same position along the length of the spindle during rotation of the spindle. That is, the second housing and the spindle would not be threadably interconnected in this case. Alternatively, the second housing may also be threadably interconnected with the spindle (i.e., both the second housing and an interfacing portion of the spindle each being threaded), such that rotation of the spindle also causes the second housing to move along the spindle. In this latter embodiment, the first and second housings simultaneously move in opposite directions along the spindle by rotating the spindle. This movement may be affected by having right hand threads for the engagement between the first housing and the spindle, and left hand threads for the engagement between the second housing and the spindle. In any case, the first and second housings may be interconnected with the patient in such a manner that increasing the spacing between the first and second housings by movement of at least one of the first and second housings along the spindle increases a magnitude of the treatment forces that are exerted on the patient. Alternatively, the first and second housings may be interconnected with the patient in such a manner that decreasing the spacing between the first and second housings by movement of at least one of the first and second housings along the spindle increases of the magnitude of the treatment forces that are exerted on the patient. Changing the spacing between the first and second housings ultimately changes the spacing between at least those locations on the patient where the first and second housings are interconnected or anchored. The orthodontic mechanical force module of the first aspect may include at least one guide pin that is slidably interconnected with both the first and second housings. Typically this will be for a palatal expansion application, although it may be appropriate for other applications as well. In this case, the first and second housings each may include a spindle aperture and a first guide pin aperture into which the spindle and a first guide pin extend. Multiple guide pin apertures could be included on both the first and second housings if multiple guide pins were used. Any such apertures in the first and second housings may be oriented so as to dispose all guide pins (including the first guide pin) and spindle in at least substantially parallel relation.

The ratchet associated with the first aspect of the present invention may include a ratchet wheel and a pawl assembly. The ratchet wheel may be included on (e.g., mounted on) or be part of the spindle. For instance, the spindle and ratchet wheel may simultaneously rotate about a common axis to change the spacing between the first and second housings as at least one of the first and second housings moves along the spindle during/from rotation of the spindle. The pawl assembly may include a pawl of the type that when engaged with the ratchet wheel, the ratchet wheel is only able to rotate in a single direction. Rotation of the ratchet wheel in the opposite direction may be realized by moving the pawl sufficiently out of engagement with the ratchet wheel. In this respect, the pawl may be characterized as being at least generally movable between first and second positions, with the ratchet wheel being rotatable only in a first direction when the pawl is in its first position, and with the ratchet wheel being rotatable in at least a second, opposite direction when the pawl is in its second position (as well as possibly in the first direction if desired/required when in this second position). The above-noted pawl assembly that may be used by the orthodontic mechanical force module of the first aspect may be biased (e.g., resiliently) into engagement with the ratchet wheel, may be of any appropriate configuration, or both. In one embodiment, the pawl is in the form of a cantilever or the like. Preferably the pawl is formed from a tempered metal to provide a desired bias toward the ratchet wheel. In one embodiment, such a pawl is within a range of ¼ hard to full hard relative to the hardness range that a spring temper alloy material is able to be hardened through induced work hardening. In another embodiment, such a pawl is within a range of about 160 KSI UTS to about 300 KSI UTS.

Integration of the above-described pawl assembly that may be used by the orthodontic mechanical force module of the first aspect may include providing first and second concave recesses (that is, a cavity formed on an exterior surface) on the pawl assembly such that a first guide pin may be at least partially seated in the first concave recess, and such that the spindle may be at least partially seated in the second concave recess. These first and second concave recesses may be disposed on opposite sides of the pawl assembly and may project in at least generally opposite directions such that at least a portion of the pawl assembly will be interposed or sandwiched between the first guide pin and the spindle. This configuration alleviates the need to fix or anchor the pawl assembly to one or both of the first guide pin and spindle.

The spindle (or any structure rotatable therewith) associated with the first aspect may include at least one, and more preferably a plurality, of through holes. Multiple through holes would preferably be disposed at the same location along the length of the spindle and so as to intersect at a center axis along which the spindle may extend. In any case, each through hole provides two apertures on an exterior surface of the spindle that could be engaged by an appropriate tool to rotate the spindle in a direction that would increase the treatment forces being exerted on the patient by changing the spacing between the first and second housings along the spindle in a predetermined manner. Preferably these apertures defined by the through hole(s) are radially spaced in at least substantially equal fashion about the circumference of the spindle and further so that at least one aperture would be available for engagement by an appropriate tool, regardless of the rotational position of the ratchet when rotation in one direction is being restrained. In one embodiment, two through holes are utilized, and these through holes are disposed perpendicular to each other, intersect at a centerline of the spindle, and are clocked relative to notches or the like on the ratchet wheel for a number of purposes. First, an end of one of these two through holes will always be disposed in the same position for engagement by an appropriate tool, regardless of the position of the ratchet when its rotational motion is being restrained in one direction. Second, an appropriate tool may be inserted though this end of the particular through hole to rotate the spindle a full 90 degrees without encountering any obstruction (e.g., any structure of the force module; any portion of the anatomy of the patient (e.g., teeth, gums, palate)). Third, such a tool may be removed from the end of the particular through hole after the noted 90 degree rotation without encountering any obstruction (e.g., any structure of the force module; any portion of the anatomy of the patient (e.g., teeth, gums, palate)) as well.

The above-noted through holes that may be used by the first aspect also may be used to deactivate the ratchet. The above-noted pawl may be disposed over at least part of one end of a through hole (e.g., the pawl may be aligned with the entirety of the through hole; the pawl may be aligned with only part of the through hole, and thereby at least partially occluding a through hole)) and in spaced relation thereto when the pawl is engaged with the ratchet wheel in a manner so as to preclude rotation of the ratchet wheel in one direction, or when the pawl is seated against the ratchet wheel in a manner so as to preclude rotation of the spindle in a direction that would reduce the magnitude of the treatment forces being exerted on the patient. This through hole may then be used to move the pawl away from the ratchet wheel to allow for bidirectional rotation of the spindle or at least to rotate in a direction so as to deactivate the ratchet (e.g., to thereby allow rotation of the spindle in a direction that would reduce the magnitude of the treatment forces being exerted on the patient). That is, an appropriate tool may be disposed into at least an end of a through hole that is opposite that end of the through hole over which the pawl is at least partially disposed in spaced relation thereto, and the tool may then be extended through the through hole and then therebeyond to engage the pawl and unseat the pawl from the ratchet wheel.

The ratchet wheel of the ratchet that may be utilized by the first aspect may be defined by a pair of bosses or flanges that are spaced along the length of the spindle, that have a larger diameter than adjacent portions of the spindle, and that include a plurality of notches or other appropriate apertures, for instance on a peripheral surface of these bosses. The pawl of the ratchet may simultaneously engage a notch on each of these bosses, or stated another way, the notches on one of the bosses may be disposed at the same radial position as the notches on the other boss. Preferably, the notches on each of the bosses are at least substantially equally spaced about the circumference of the peripheral surface of the bosses. One or more of the above-described through holes may be located between the noted pair of bosses and for one or more of the above-described purposes. Other ratchet wheel configurations may be appropriate, although the configuration described herein provides a number of advantages.

There is a preferred configuration for that peripheral surface(s) of the ratchet wheel on which the pawl "rides" in the case of the first aspect when providing the ratcheting function. Although this feature will be described in relation to the above-described pair of bosses, it is applicable to other ratchet wheel configurations as well. Generally, the plurality of radially spaced notches on the peripheral surface of each boss may be separated by an arcuate surface. Each such arcuate surface may be characterized as a transition section. In one embodiment, each transition section is defined by a common radius that is located along the centerline of the spindle. The pawl will then ride on a transition section on each boss when proceeding from one notch to the next during rotation of the spindle in a direction that provides for an increase in treatment forces. The notches on each boss may be configured such that the pawl will momentarily lose contact with the bosses when "dropping" into the next notch on each boss. This will preferably make a discernible sound that may be used when making an adjustment of the force module (e.g., to signify a predetermined amount of rotation of the spindle has been achieved). Although various notch configurations may allow the pawl to momentarily lose contact to make such a discernible sound, in one embodiment each notch on each boss is defined by a pair of at least generally flat surfaces that are disposed at least generally perpendicular to each other. Moreover, the flat surface of a given notch that follows a transition section in the direction of rotation of the spindle when increasing treatment forces may extend at least generally toward the centerline of the spindle. This provides a "drop off" of sorts between this transition section and the other flat surface of the corresponding notch onto which the pawl "drops" to again make a discernible sound.

The above-noted bosses that may be utilized by the first aspect may provide other functions than as a ratchet wheel. The bosses may be used to limit the translation of a first guide pin of the above-described type along its length dimension. In this regard, the first guide pin may include a collar that is retained between the pair of bosses on the spindle. This collar may have a larger diameter than adjacent portions of the first guide pin, those portions of the first guide pin that are slidably engaged with the first and second housings, or both. Moreover, the bosses may function to locate the pawl assembly relative to the spindle in the length dimension. For instance, the pawl assembly may include a pair of legs that are spaced so that the noted pair of bosses may be located therebetween. A pair of oppositely disposed surfaces of each of these legs may then include the above-noted first and second concave recesses.

A second aspect of the present invention is embodied by an orthodontic mechanical force module that includes first and second housings. Both the first housing and second housings are rotatably interconnected with a spindle. That is, the spindle is able to rotate relative to both the first and second housings. At least one of the first and second housings is also threadably interconnected with the spindle so as to move along the spindle during/from rotation of the spindle. That is, at least one of the first and second housings is threaded, along with at least a segment of the spindle. Movement of at least one of the first and second housings along the spindle changes the relative position between the first and second housings along the spindle, and thereby the treatment forces being exerted on the patient. A plurality of detent apertures are associated with the spindle and are radially spaced about an axis (e.g., a rotational axis of the spindle). A detent engages one of these detent apertures as the spindle rotation causes any one detent aperture to move into alignment with the detent. There also is a plurality of adjustment or activation apertures associated with the spindle that are also radially spaced about the same axis as the detent apertures and into which a tool may be inserted to rotate the spindle. However, these adjustment apertures are spaced along the length dimension of the spindle from the detent apertures and are thereby separate structures from the detent apertures. Stated another way, the adjustment apertures and the detent apertures are not disposed along a common line that extends about the circumference of the spindle.

Various refinements exist of the features noted in relation to the subject second aspect of the present invention. Further features may also be incorporated in the subject second aspect of the present invention as well. These refinements and additional features may exist individually or in any combination. The orthodontic mechanical force module of the second aspect may include a ratchet wheel that is mounted on or is part of, and in any case rotatable with, the spindle. This orthodontic mechanical force module may further include a pawl that is at least engageable with the ratchet wheel to prevent rotation of the same in one direction when appropriately engaged therewith, but which will allow rotation of the ratchet wheel in the opposite direction even when the pawl is engaging the ratchet wheel. The plurality of detent apertures may be disposed on the ratchet wheel and the pawl may correspond with a detent.

The ratchet wheel that may be associated with the orthodontic mechanical force module of the second aspect may be defined by a pair of bosses that are spaced along the spindle and that include a plurality of notches on a peripheral surface thereof to define the detent apertures. The pawl may simultaneously engage a notch on each of these bosses. Moreover, the noted adjustment apertures may be disposed between this pair of bosses. In the case where the adjustment apertures are in the form of through holes, an appropriate tool may be inserted through one end of a particular through hole and beyond its opposite end to sufficiently unseat the pawl from the ratchet wheel to allow bi-directional rotation of the ratchet wheel. When engaged with the ratchet wheel to allow only one directional rotation of the ratchet wheel, the pawl may be disposed in spaced relation to, but at least partially aligned with, at least one of the through holes to facilitate this type of unseating of the pawl from the ratchet wheel.

The pawl that may be utilized by the orthodontic mechanical force module of the second aspect may be biased into engagement with the ratchet wheel. The interface between the pawl and the ratchet wheel may be such that the pawl at least substantially directly and mechanically opposes rotation of the ratchet wheel in one direction when engaged with at least one of the notches of the ratchet wheel. In one embodiment and for purposes of providing this type of mechanical opposition, the pawl is disposed within 20 degrees of a tangent to a peripheral surface of the ratchet wheel at a location that is between adjacent pairs of notches on the ratchet wheel. Stated another way and again for purposes of providing the above-noted type of mechanical opposition, the pawl may be disposed relative to the ratchet wheel so as to be disposed at an angle from about 70 degrees to about 110 degrees relative to an imaginary radius line extending outwardly from a center of the spindle to the point of engagement between the pawl and the ratchet wheel to preclude rotation in one direction (but not in the opposite direction).

The plurality of radially spaced adjustment apertures utilized by the orthodontic mechanical force module of the second aspect may be in the form of a pair of through holes that extend entirely through the spindle, that intersect at a centerline of the spindle, and that are disposed in perpendicular relation to each other. This would then provide four adjustment apertures that were each separated by a radial spacing of 90 degrees. Preferably, these four adjustment apertures are clocked relative to the plurality of detent apertures such that: 1) one adjustment aperture will be disposed at the same position for engagement by an appropriate adjusting tool, regardless of which detent aperture is being engaged by the detent to restrict rotation of the spindle in one direction; and 2) this same adjustment aperture will be disposed so as to allow for a full 90 degrees of rotation of the spindle with an appropriate tool and for subsequent removal of the tool after the rotation, all without encountering an obstruction between the adjusting tool and any portion of the force module, and as such, a full 90 degrees of rotation can be accomplished without having to remove and re-insert the activation tool.

The various features discussed above in relation to the first aspect of the present invention may be utilized by this second aspect of the present invention as well. In addition, the various features discussed in relation to this second aspect may be utilized by the first aspect as well.

A third aspect of the present invention is embodied by an orthodontic mechanical force module that includes first and second housings. A rotatable spindle is rotatably interconnected with both the first and second housings. At least one of the first and second housings is also threadably interconnected with the spindle as well. Rotation of the spindle thereby causes at least one of the first and second housings to move along the spindle while the spindle rotates relative to both the first and second housings. At least one through hole is provided on the spindle (which includes any structure that rotates therewith). The spindle includes a ratchet wheel that interacts with a pawl. At least when the pawl is engaged with the ratchet wheel so as to preclude rotation of the ratchet wheel in one direction, the pawl is disposed in at least partially overlying and spaced relation to the through hole. That is, at least a portion of the pawl is disposed vertically beyond that portion of the exterior surface of the spindle on which an adjacent end of the noted through hole is disposed (the "adjacent end" being that end of the through hole that is closest to the overlying pawl). The pawl may then be characterized as at least partially occluding this adjacent end of the noted through hole. Such a through hole may then be used for one or more of the above-noted purposes discussed in relation to the first aspect. Moreover, the various features discussed above in relation to one or both of the first and second aspects may be used individually or in any combination in relation to this third aspect of the present invention as well, and vice versa.

A fourth aspect of the present invention is embodied by a method of operating an orthodontic mechanical force module installed on a patient. This method includes increasing a magnitude of a treatment force being exerted on the patient by the orthodontic mechanical force module using a first tool. This method also includes decreasing the magnitude of the treatment force being exerted on the patient by the orthodontic mechanical force module using a second tool that is structurally different from the first tool in at least one respect.

Various refinements exist of the features noted in relation to the subject fourth aspect of the present invention. Further features may also be incorporated in the subject fourth aspect of the present invention as well. These refinements and additional features may exist individually or in any combination. The first tool may be configured such that it would not be able to be used to reduce the magnitude of the treatment forces being exerted on the patient. Consider a protocol where a caregiver is provided with the first tool and not the second tool, and where the treating practitioner retains the second tool. This allows the caregiver to at least assist in the execution of a treatment plan by increasing the treatment forces being exerted on the patient, typically on some repeating basis (e.g. nightly). However, since the caregiver does not have the second tool, the caregiver would not be able to reduce the magnitude of the treatment forces. Instead, any such reduction in the treatment forces would require an office visit of sorts, where the practitioner would use the retained second tool to reduce the magnitude of the treatment forces being exerted on the patient. In the case of the orthodontic mechanical force module of the first aspect having at least one through hole on the spindle for purposes of moving the pawl away from the ratchet wheel, the first tool of this fourth aspect may include a stop that prevents the first tool from being inserted far enough within a given through hole to move the pawl out of engagement with the ratchet wheel. However, the second tool would be insertable sufficiently through a given through hole so as to be able to engage the pawl and move the pawl out of engagement with the ratchet wheel.

Increasing the magnitude of the treatment forces in the case of the fourth aspect may include changing a spacing between a pair of housings of the orthodontic mechanical force module along a spindle of the orthodontic mechanical force module in one manner, while decreasing the magnitude of the treatment forces may include changing the spacing between this pair of housings along the spindle in an opposite manner. For instance, if the treatment forces are increased by increasing the spacing between the pair of housings, the treatment forces may be reduced by reducing the spacing between the pair of housings. Similarly, if the treatment forces are increased by decreasing the spacing between the pair of housings, the treatment forces may be reduced by increasing the spacing between the pair of housings. Changing the spacing between the noted pair of housings along the spindle may include moving one or both of these housings along the spindle, for instance in the manner discussed above in relation to the first aspect.

A fifth aspect of the present invention is embodied by a method of operating an orthodontic mechanical force module. This method includes changing a spacing between first and second housings of the module along a spindle of the module in one manner using a first tool to rotate the spindle in a first direction, and changing a spacing between the first and second housings along the spindle in an opposite manner using a second tool to rotate the spindle in a second direction that is opposite the first direction. The second tool is structurally different from the first tool in at least one respect.

Various refinements exist of the features noted in relation to the subject fifth aspect of the present invention. Further features may also be incorporated in the subject fifth aspect of the present invention as well. These refinements and additional features may exist individually or in any combination. The spacing between the first and second housings may dictate the magnitude of the treatment forces being exerted on the patient. Increasing the magnitude of the treatment forces in the case of the fifth aspect may include moving at least the first housing along a spindle in one manner, while decreasing the magnitude of the treatment forces may include moving at least the first housing along the spindle in an opposite manner. For instance, if the treatment forces are increased by increasing the spacing between the first and second housings, the treatment forces may be reduced by reducing the spacing between the first and second housings. Similarly, if the treatment forces are increased by decreasing the spacing between the first and second housings, the treatment forces may be reduced by increasing the spacing between the first and second housings.

The first tool associated with the subject fifth aspect may be configured such that it would only be able to rotate the spindle in one direction, but not in the opposite direction. Consider a protocol where a caregiver is provided with the first tool and not the second tool, and where the treating practitioner retains the second tool. This allows the caregiver to at least assist in the execution of a treatment plan by increasing the treatment forces being exerted on the patient, typically on some repeating basis (e.g. nightly). However, since the caregiver does not have the second tool, the caregiver would not be able to reduce the magnitude of the treatment forces. Instead, any such reduction in the treatment forces would require an office visit of sorts, where the practitioner would use the retained second tool to reduce the magnitude of the treatment forces being exerted on the patient. In the case of the orthodontic mechanical force module of the first aspect having at least one through hole on the spindle for purposes of moving the pawl away from the ratchet wheel, the first tool of this fifth aspect may include a stop that prevents the first tool from being inserted far enough within a given through hole to move the pawl out of engagement with the ratchet wheel. However, the second tool would be insertable sufficiently through a given through hole so as to be able to engage the pawl and move the pawl out of engagement with the ratchet wheel.

A sixth aspect on the present invention is embodied by a method for operating an orthodontic mechanical force module that includes a spindle and a first housing. The spindle is rotated in a first direction to move the first housing along the spindle. The orthodontic mechanical force module may be disposed in a first mode to provide a greater resistance to a rotation of the spindle in a second direction than in the noted first direction. This resistance to a rotation of the spindle in the second direction may be provided by a ratchet of the type discussed above in relation to the first aspect, in which case the magnitude of resistance to rotation in the second direction may be one that precludes rotation of the spindle in the second direction absent a failure of the ratchet. The module may also be disposed in a second mode to provide at least substantially the same magnitude of resistance (including no substantial resistance) to rotation of the spindle in both the first and second directions.

A seventh aspect of the present invention is embodied by a method of assembling or disassembling an orthodontic mechanical force module. A spindle and pawl assembly of the orthodontic mechanical force module are disposed in a predetermined positional relationship relative to each other. This pawl assembly includes a pawl and a ratchet wheel. The pawl is forced out of engagement with the ratchet wheel to a degree where the ratchet wheel may rotate in either direction. First and second housings of the module are positioned on first and second ends of the spindle, respectively, while the pawl is sufficiently disengaged from the ratchet wheel to allow rotation in either direction. The movement of at least one of the first and second housings relative to the spindle is thereafter affected by rotation of the spindle relative to the first and second housings. One or more fixtures may be utilized by this seventh aspect to facilitate the execution of one or more of the steps of this seventh aspect. One or more of such fixtures could be adapted or configured to accommodate the entire structure of the force module, for instance any guide pin(s) utilized by the force module.

An eighth aspect of the present invention is embodied by a method for executing an orthodontic treatment. An orthodontic mechanical force module is anchored to a patent at two different locations within the patient's mouth (e.g. to two different teeth; to two different groups of teeth). The module includes a spindle and first and second housings that are both mounted on and movably interconnected with the spindle. Rotation of the spindle moves at least the first housing along the spindle to change the spacing between the first and second housings, to in turn change the treatment force being exerted on the patient. Instructions are provided regarding a treatment plan to be executed for the patient, where the treatment plan includes undertaking a plurality of spaced-in-time activations of the module (e.g., done by a parent). In the case where treatment forces are increased by increasing the spacing between the first and second housings, each activation of the module in relation to the eighth aspect entails rotating the spindle in a first direction using a first tool to increase the spacing between the first and second housings. An assessment of the patient is done (e.g., by an orthodontist) at some point in time after the instructions were provided as to the treatment plan to be followed. This assessment may be done knowing that the spindle has not been rotated in a second direction using the first tool, at any time after the instructions were provided, to achieve a spacing between the pair of housings that is less than a spacing between the pair of housings from an immediately preceding (in time) activation. Rotation of the spindle in the second direction in this case would decrease the spacing between the pair of housings, and thereby the treatment forces being exerted on the patient. Stated another way, the first tool may not be used to reduce the treatment forces from that which was provided from the most recent activation of the module.

In the case where treatment forces are increased by decreasing the spacing between the first and second housings, each activation of the module in relation to the eighth aspect entails rotating the spindle in a first direction using a first tool to decrease the spacing between the first and second housings. An assessment of the patient is done (e.g., by an orthodontist) at some point in time after the instructions were provided as to the treatment plan to be followed. This assessment also may be done knowing that the spindle has not been rotated in a second direction using the first tool, at any time after the instructions were provided, to achieve a spacing between the pair of housings that is more than a spacing between the pair of housings from an immediately preceding (in time) activation. Rotation of the spindle in the second direction in this case would increase the spacing between the pair of housings, and thereby decrease the treatment forces being exerted on the patient. Stated another way, the first tool may not be used to reduce the treatment forces from that which was provided from the most recent activation of the module.

A ninth aspect of the present invention is embodied by a method for executing an orthodontic treatment. An orthodontic mechanical force module is anchored to a patent at two different locations within the patient's mouth (e.g. to two different teeth; to two different groups of teeth). The module includes a spindle and first and second housings that are both mounted on and movably interconnected with the spindle. Rotation of the spindle moves at least the first housing along the spindle to change the spacing between the first and second housings, to in turn change the treatment force being exerted on the patient. A certain amount of rotation of the spindle at a given time may be characterized as an activation. At least one activation of the module of this nature is undertaken. A tactile indication is provided of an attempt to rotate the spindle in the second direction or at least of an attempt to rotate the spindle in a second direction more than a predetermined amount (e.g., to rotate the spindle through a distance corresponding with a spacing between notches of a ratchet wheel associated with the spindle). The second direction is opposite the first direction, and would thereby tend to move the first and second housings relative to each other in a direction that would tend to reduce the magnitude of the treatment forces being exerted on the patient.

DETAILED DESCRIPTION

Figure 1:
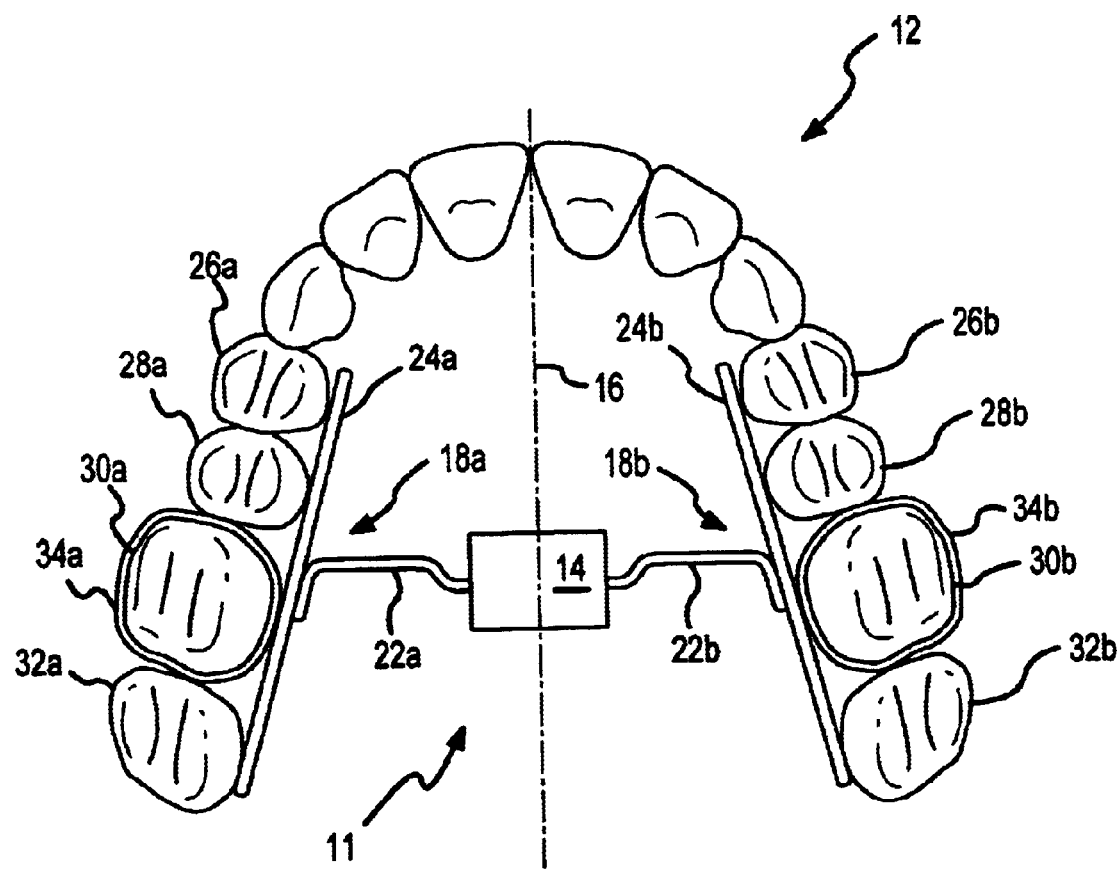
FIG. 1 is a schematic, plan view of one embodiment of a palatal expansion device mounted on an upper dental arch.

The present invention will now be described in relation to the accompanying drawings which at least assist in illustrating its various pertinent features. FIG. 1 generally illustrates a palatal expansion device 11 that is installed on an upper dental arch 12 of a patient and which may be used in combination with one or more other orthodontic appliances to execute a desired treatment. The palatal expansion device 11 is generally located between the patient's tongue and the palate of the patient. Sometimes this is referred to as the "vault" of the patient's mouth. In any case, the palatal expansion device 11 is anchored to the dental arch 12 on both sides of a midline 16 of the arch 12 so as to allow for increasing the width or lateral extent of the arch 12. This is commonly referred to the art as palatal expansion. Teeth on one side of the midline 16 utilize an "a" designation, while teeth on the opposite side of the midline 16 utilize a "b" designation.

The palatal expansion device 11 generally includes an orthodontic mechanical force module 14 and a pair of anchor assemblies 18a and 18b. The orthodontic mechanical force module 14 is only schematically illustrated in FIG. 1, but is illustrated in more detail below in relation to FIGS. 2–10. However, generally the orthodontic mechanical force module 14 includes a pair of movable portions that are typically used in the case of the palatal expansion device 11 to increase the width of the dental arch 12 or to affect palatal expansion. In this regard, the anchor assembly 18a is associated with the "a" side of the dental arch 12 in the illustrated embodiment, while the anchor assembly 18b is associated with the "b" side of the dental arch 12 in the illustrated embodiment. Although the anchor assembly 18a is the mirror image of the anchor assembly 18b in the illustrated embodiment, such need not be the case for all treatments.

Each anchor assembly 18 extends between and is fixed to a movable portion of the orthodontic mechanical force module 14 and to one or more teeth in the dental arch 12. Any way of interconnecting each anchor assembly 18 with the dental arch 12 may be utilized. However, in the illustrated embodiment each anchor assembly 18 includes a band 34, a lingual wire segment 24, and a wire segment 22. The band 34 of a given anchor assembly 18 is mounted on a first molar 30 on one side of the dental arch 12. The lingual wire segment 24 of a given anchor assembly 18 is fixed to the corresponding band 34 in any appropriate manner (e.g., soldering; brazing; welding) and generally interfaces with the corresponding buccal segment and molar or posterior segment of the arch 12. More specifically, the lingual wire segment 24 of a given anchor assembly 18 in the illustrated embodiment interfaces with the buccal or lingual side of a first bicuspid 26, a second bicuspid 28, a first molar 30, and a second molar 32 on one side of the dental arch 12.

The wire segment 22 of a given anchor assembly 18 is fixed to the corresponding lingual wire segment 24 and/or band 34 in any appropriate manner (e.g., soldering; brazing; welding). The wire segment 22 of a given anchor assembly 18 is also fixed to one of the movable portions of the orthodontic mechanical force module 14 as noted and in any appropriate manner (e.g., soldering; brazing; welding). Movement of the movable portions of the orthodontic mechanical force module 14 in a manner that is at least generally transverse to the midline 16 in the illustrated embodiment exerts a force on a number of teeth on opposite sides of the dental arch 12, through the respective anchor assemblies 18a, 18b, to affect an expansion of the arch 12 or to increase the width of the arch 12.

The manner in which the orthodontic mechanical force module 14 is interconnected with two different locations on a patient is not of particular significance in relation to the present invention. Any appropriate manner of interconnecting the orthodontic mechanical force module 14 with at least two different locations on a particular patient may be utilized in relation to the orthodontic mechanical force module 14. What is of importance is the structure and operation of the orthodontic mechanical force module 14. Generally and as will now be discussed in more detail, the orthodontic mechanical force module 14 may be used in any orthodontic or dental application where it is desired to change a certain spacing associated with the teeth of a patient. Although the orthodontic mechanical force module 14 is anticipated to be used primarily for increasing such a spacing, there may be applications where it would be appropriate to use the force module 14 to generate contractive forces to reduce spacing between two teeth or two groups of teeth of a patient's dental arch.

Figure 2:
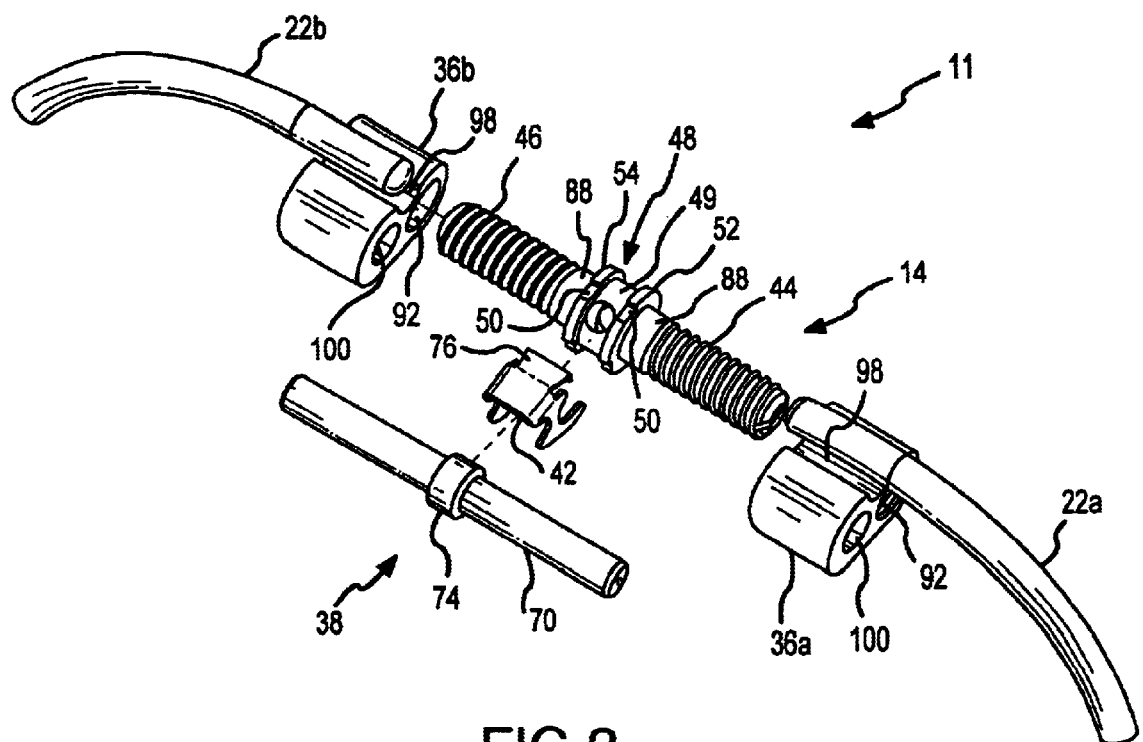
FIG. 2 is an exploded, perspective view of a portion of the palatal expansion device of FIG. 1 with one embodiment of an orthodontic mechanical force module therefor.
Figure 3:
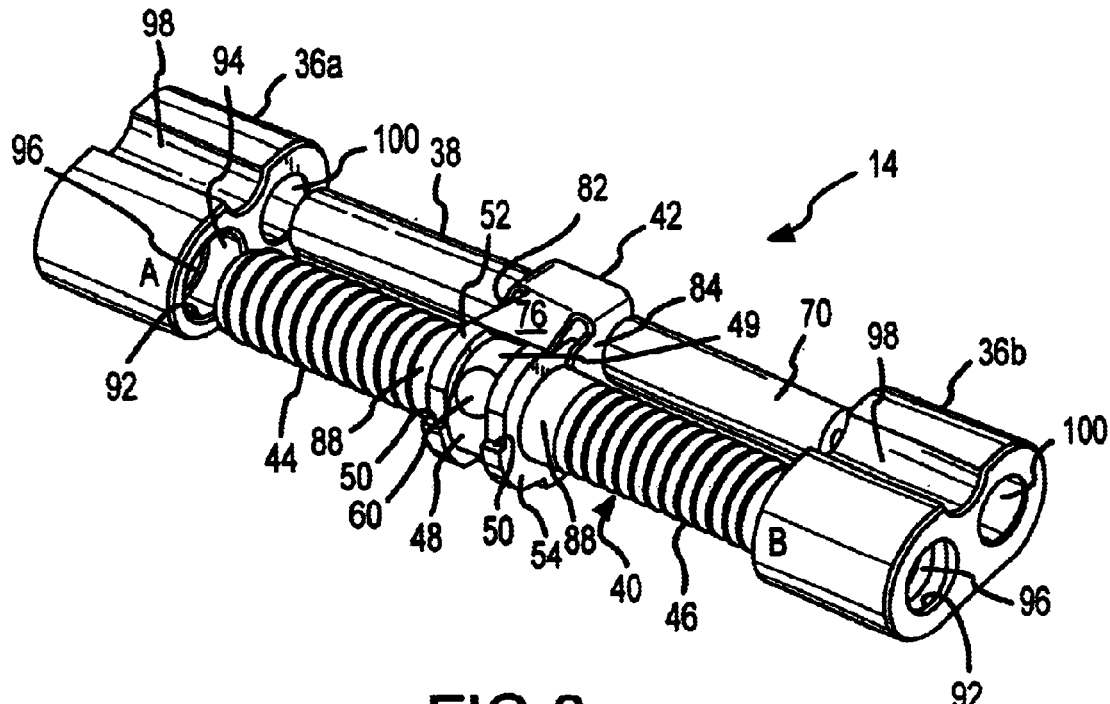
FIG. 3 is an enlarged, perspective view of the orthodontic mechanical force module used by the palatal expansion device of FIG. 2, prior to installing the pair of housings on opposite ends of a guide pin and spindle of the orthodontic mechanical force module.
Figure 4:
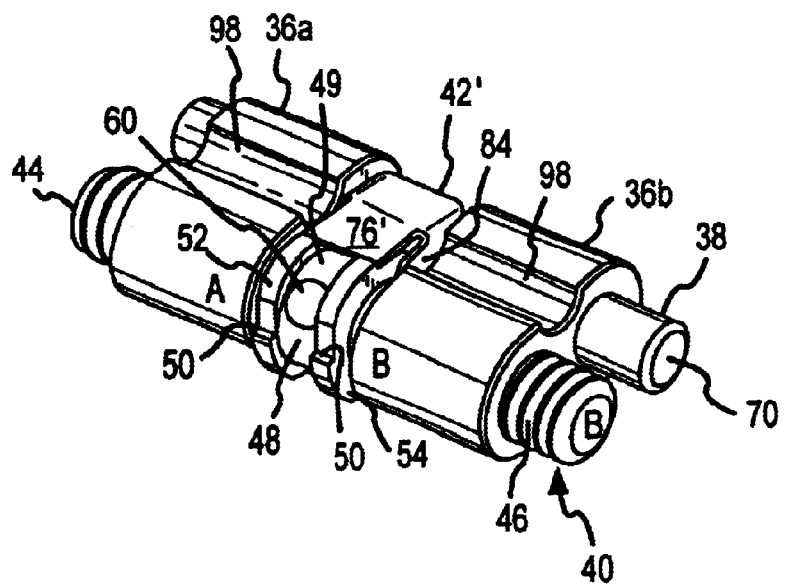
FIG. 4 is a perspective view of the orthodontic mechanical force module of FIG. 3, with the pair of housings being fully mounted on the guide pin and spindle, and a utilizing an alternate configuration for a pawl of a pawl assembly of the orthodontic mechanical force module.

Reference will now be made to FIGS. 2–3. There the orthodontic mechanical force module 14 is illustrated as generally including first and second housings 36a, 36b, respectively, a guide pin assembly 38, a spindle 40, and a pawl assembly 42. The wire segment 22a of the anchor assembly 18a of the palatal expansion device 11 of FIG. 1 will typically be fixed to the first housing 36a in any appropriate manner, while the wire segment 22b of the anchor assembly 18b of the palatal expansion device 111 of FIG. 1 will typically be fixed to the second housing 36b in any appropriate manner. The first and second housings 36a, 36b are slidably mounted on the guide pin assembly 38, and are threadably engaged with the spindle 40. Rotation of the spindle 40 in one direction and in a manner discussed in more detail below increases the spacing between the housing 36a, 36b, which in turns attempts to increase the spacing between the anchor assemblies 18a, 18b, which in turn exerts an expansion force on opposite sides of the dental arch 12 for the palatal expansion application illustrated in FIG. 1. In the event that the wire segment 22a of the anchor assembly 18a were to be fixed to the second housing 36b and in the event that the wire segment 22b of the anchor assembly 18b were to be fixed to the first housing 36a (i.e., a "cross-over or "cross-connect" configuration), rotation of the spindle 40 in one direction and in a manner discussed in more detail below would decrease the spacing between the housing 36a, 36b, which in turns attempts to increase the spacing between the anchor assemblies 18a, 18b, which in turn exerts an expansion force on opposite sides of the dental arch 12 for the palatal expansion application illustrated in FIG. 1.

Figure 7:
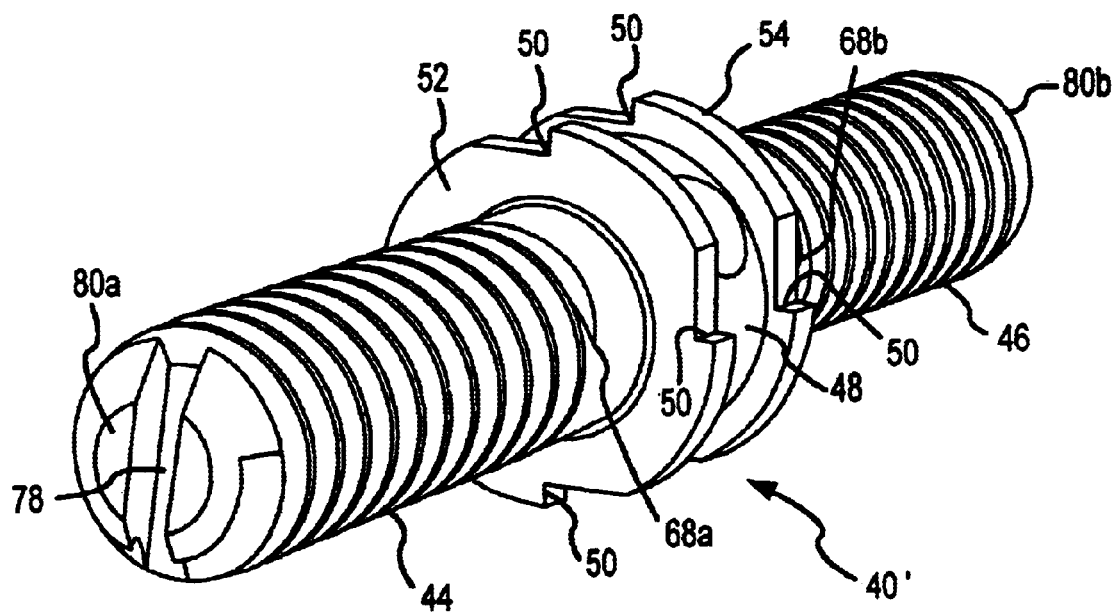
FIG. 7 is a perspective view of a spindle for the orthodontic mechanical force modules of FIGS. 3 and 13, having an optional adjustment slot disposed on an end thereof.
Figure 10:
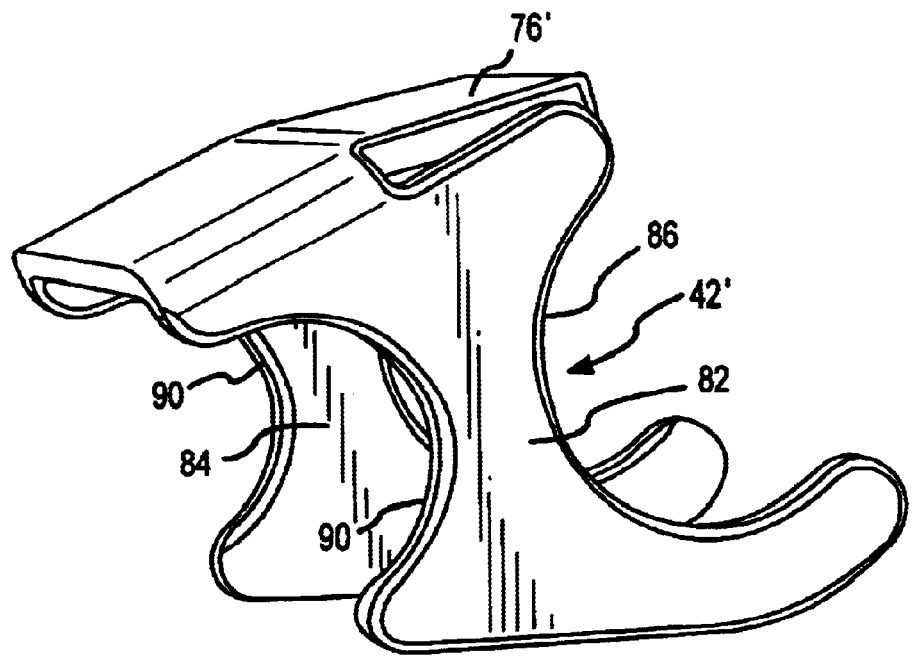
FIG. 10 is a perspective view of the pawl assembly used by the orthodontic mechanical force module of FIG. 3.

Various details regarding the spindle 40 of the orthodontic mechanical force module 14 are illustrated in FIGS. 2–8. FIG. 7 includes an additional feature in relation to the spindle 40 that will be discussed in more detail below, and therefore a "single prime" designation is used in relation thereto. Generally, the spindle 40' of FIG. 7 includes a slot 78 that is formed on at least one of the two ends 80 of the spindle 40' and which may be used to facilitate the assembly of the orthodontic mechanical force module 14. In one embodiment, the slot 78 is formed on only one end of the spindle 40', which allows the same to be used as a visual identifier for facilitating the assembly of the force module 14 as well (e.g., to identify the relevant end of the spindle 40' and which housing 36a, 36b should be installed thereon).

The spindle 40 of FIGS. 2–8 generally includes a first threaded section 44, a second thread section 46, and an actuating head 48 positioned therebetween. This actuating head 48 of the spindle 40 may be separately attached to the spindle 40 or an integral part thereof, but in any case rotates with the spindle 40. The actuating head 48 includes a plurality of radially spaced notches 50, and therefore the actuating head 48 may also be characterized as a ratchet wheel or the like. Any appropriate number of notches 50 may be utilized, and any appropriate spacing may be used between adjacent pairs of notches 50. Preferably, the notches 50 are equally spaced about the periphery of the actuating head 48. These notches 50 cooperate with the pawl assembly 42 to control the rotational position of the spindle 40 in a manner that will be discussed in more detail below. The notches 50 are actually formed on the periphery of first and second bosses or flanges 52, 54, respectively, of the actuating head 48 of the spindle 40. These flanges 52, 54 are annular and extend radially beyond the first and second threaded sections 44, 46, respectively, of the spindle 40. A smooth cylindrical section 88 separates the flange 52 from the first threaded section 44, while another smooth cylindrical section 88 separates the flange 54 from the second threaded section 46.

Figure 8:
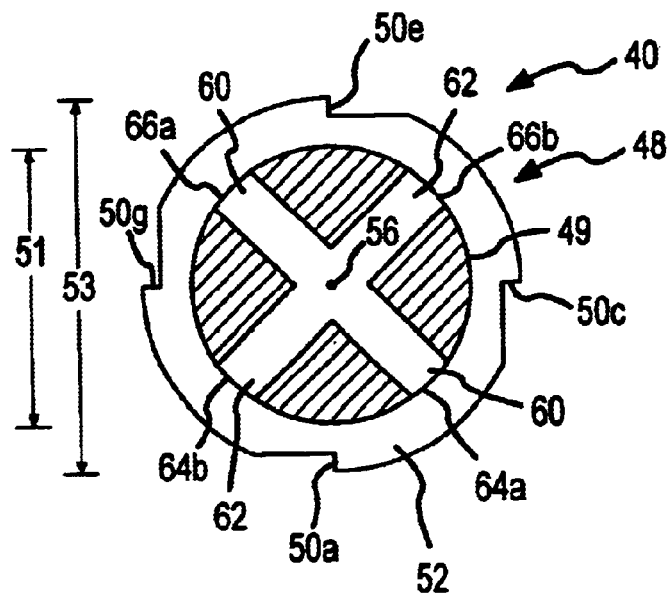
FIG. 8 is a cross-sectional view of the spindle of FIG. 6, taken along line 8—8.

Both flanges 52, 54 have the same diameter in the illustrated embodiment. Only the flange 52 is illustrated in FIG. 8, where there it can be seen that its diameter 53 is also greater in magnitude than a diameter 51 of a medial portion 49 of the actuating head 48 that is located between the first and second flanges 52, 54. In any case, the first flange 52 is laterally spaced from the second flange 54, or stated another way the flanges 52, 54 are spaced along the length or length dimension of the spindle 40. That is, the first flange 52 is separated from the second flange 54 along a direction that is substantially parallel with a central reference axis 56 of the spindle 40. Moreover, each particular notch 50 of the first flange 52 has a substantially similar radial location, with respect to the spindle 40, as each corresponding notch 50 of the second flange 54. As such, the pawl assembly 42 simultaneously engages a notch 50 on each of the flanges 52, 54. In one embodiment and referring to FIG. 6, an imaginary line 58 connecting notch 50a of the first flange 52 and notch 50b of the second flange 54 is substantially parallel to the central reference axis 56 of the spindle 40. As shown in FIG. 8, these radially spaced notches 50 of the actuating head 48 are preferably equidistantly spaced from adjacent notches 50 about the circumference or annular extent of the spindle 40. In other words, the radial distance between notch 50a and notch 50c is substantially identical to a radial distance between notch 50c and notch 50e, and so forth. However, as noted above any desired/required spacing may be utilized.

Still referring to FIGS. 2–8, besides the four notches 50 positioned on each of the first and second flanges 52, 54, the actuating head 48 of the spindle 40 has first and second adjustment holes 60, 62 that each extend through an entirety of the spindle 40, namely through the medial portion 49. Both of these adjustment holes 60, 62 also preferably pass through the central reference axis 56 of the spindle 40. Moreover, these adjustment holes 60, 62 intersect with one another in a substantially perpendicular fashion. As illustrated, each of the adjustment holes 60, 62 has a first opening 64 and a second opening 66 on an exterior surface of the medial portion 49 of the actuating head 48 of the spindle 40. These openings 64, 66 of the adjustment holes 60, 62 are positioned so that an opening (e.g., 64a) is radially interposed substantially midway between two adjacent notches (e.g., 50a and 50c) of the actuating head 48 in the illustrated embodiment. These adjustment holes 60, 62 may be used to change the rotational position of the spindle 40, and thereby the spacing between the housings 36a, 36b, in a manner that will be discussed in more detail below. Notwithstanding the benefits of having an adjustment aperture spaced every 90 degrees about the spindle 40, other adjustment aperture spacings may be utilized.

Preferably there is a certain relationship between the notches 50 and the adjustment holes 60, 62. In the illustrated embodiment, the adjustment holes 60, 62 are clocked relative to the notches 50 on the bosses 52, 54 such that one end of either of the adjustment holes 60, 62 will be disposed at the same position for engagement by an appropriate adjustment tool (discussed below in relation to FIGS. 11–12), regardless of which pair of notches 50 on the bosses 52, 54 is being engaged by the pawl assembly 42 to restrict rotation of the spindle 40 in an undesired direction. Further, the adjustment holes 60, 62 are clocked relative to the notches 50 on the bosses 52, 54 such that one end of either of the adjustment holes 60, 62 will be disposed so as to allow for 90 degrees of rotation of the actuating head 48 and spindle 40 without encountering any obstruction both during this rotation and during any subsequent removal of the tool that was used to make the rotational adjustment, regardless of which pair of notches 50 on the bosses 52, 54 is being engaged by the pawl assembly 42 to restrict rotation of the spindle 40 in an undesired direction.

The spindle 40 includes first and second threaded sections 44, 46 that are disposed on opposite sides of its actuating head 48. Generally, one of the first and second threaded sections 44, 46 of the spindle 40 is a "left-hand" thread system, while the other of the first and second threaded sections 44, 46 of the spindle 40 is a "right-hand" thread system. As such, rotation of the spindle 40 in one direction simultaneously moves the first and second housings 36a, 36b in opposite directions along the spindle 40 (either toward or away from each other, depending upon the direction of rotation). Moreover, the threaded sections 44, 46 are likewise "clocked." That is, the origin 68a (FIG. 7) of the thread system of the first threaded section 44 and the origin 68b of the thread system of the second threaded section 46 occur at the same radial position on the spindle 40. In other words, a line connecting origins 68a, 68b would be substantially parallel to the central reference axis 56 of the spindle 40 as well. This feature, combined with the corresponding internal thread orientation of the housings 36a, 36b and which will be discussed in more detail below, may generally enable both housings 36a, 36b to be retracted (i.e., moved toward the actuating head 48) so that they at least substantially simultaneously abut the respective flanges 52, 54 of the actuating head 48. Moreover, this clocking of the first and second threaded sections 44, 46 also enables the housings 36 to be expanded evenly (i.e., moved away from the actuating head 48 the same distance). Furthermore, this clocking feature also allows the housings 36a, 36b to expand evenly to their widest possible configuration, and to then approximately simultaneously discontinue their threaded engagement with the spindle 40. Summarily, due at least in part to the clocking of the threaded sections 44, 46 of the spindle 40 in the noted manner, each of the first and second housings 36 will be substantially equidistantly spaced from the actuating head 48 at all times. Accordingly, regardless of the amount of rotation applied to the spindle 40, the first and second housings 36a, 36b of the force module 14 will be disposed equidistantly from the actuating head 48. It should be appreciated that if any degree of asymmetry was desired/required for a given orthodontic treatment, the orthodontic mechanical force module 14 could be adapted to accommodate the same.

The guide pin assembly 38 of the orthodontic mechanical force module 14 is illustrated in FIGS. 2–6 and includes at least one guide pin 70. One guide pin 70 is used by the illustrated embodiment. Two or more guide pins 70 also could be utilized, with one being disposed on each side of the spindle 40 (not shown). In any case, the guide pin 70 is generally substantially aligned with a length of the spindle 40. In other words, a central reference axis 72 of the guide pin 70 is at least substantially parallel with the central reference axis 56 of the spindle 40. In addition, the guide pin 70 and the spindle 40 are also preferably at least substantially equal in length. However, such need not be the case in all instances.

The guide pin 70 includes an annular protrusion or collar 74 that is positioned between the first and second flanges 52, 54 of the actuating head 48 of the spindle 40. The collar 74 of the guide pin 70 may be separated from at least one of the first and second flanges 52, 54 of the actuating head 48 by a relatively small distance, which in one embodiment is within a range of about 0.001 inch up to about 0.003 inch. However, yet other embodiments may exhibit other appropriate distances of separation between the collar 74 of the guide pin 70 and the flanges 52, 54 of the actuating head 48. In any case, having the collar 74 between the flanges 52, 54 of the actuating head 48 generally enables the spindle 40 to restrict the guide pin 70 from significant movement in a direction that is at least generally parallel to or along its central reference axis 72. Nevertheless, while clearance between the collar 74 and the flanges 52, 54 is intended to be very close, preferably the clearance between the same does not significantly impede the ability to rotate the spindle 40.

The guide pin 70 slidably interfaces with each of the housings 36a, 36b, while the spindle 40 is threadably engaged with each of the housings 36a, 36b. In this regard and referring to FIGS. 2–4, as well as FIG. 9, these housings 36a, 36b are each equipped with at least one guide bore 100 designed to be slidingly engaged by the guide pin assembly 38. Each housing 36a, 36b would include one guide bore 100 for each guide pin 70 used by the orthodontic mechanical force module 14. Each of these guide bores 100 preferably has a substantially smooth surface to provide a "slip fit" or the like for the guide pin assembly 38. Annular clearance between each guide bore 100 and the associated guide pin 70 is preferably kept to a minimum (e.g., about 0.0008 inch) to keep the guide pin 70 in at least substantially parallel relation with the spindle 40. However, any appropriate relative spacing may be utilized that provides the functionality described herein.

Each of housings 36a, 36b also has at least one adjustment bore 92 designed to be engaged by the respective threaded section 44, 48 of the spindle 40. Each of the adjustment bores 92 of these housings 36a, 36b is illustrated as having a non-threaded portion 94 (e.g., a smooth cylindrical surface, preferably of the same length as the smooth cylindrical sections 88 to be able to realize the position illustrated in FIG. 6) that is positioned toward the actuating head 48 of the spindle 40, and a threaded portion 96 that is positioned most remote from the actuating head 48 of the spindle 40 in the assembled condition. The functionality of the non-threaded portions 94 of the adjustment bores 92 becomes evident once the orthodontic mechanical force module 14 has been expanded to its maximum degree. While the threaded portion 96 of each adjustment bore 92 will disengage with the respective threaded section 44, 46 of the spindle 40 at this point, the non-threaded portion 94 of each adjustment bore 92 enables the respective threaded section 44, 46 of the spindle 40 to remain circumferentially contained within each of the housings 36a, 36b. Since the spindle 40 and the guide pin 70 are generally of the same length, this also serves to keep the ends of the guide pin 70 still sufficiently engaged within the guide bores 100 of the housings 36a, 36b to maintain relative alignment between the spindle 40 and the guide pin 70. Thus, providing each adjustment bore 92 within a non-threaded portion 94 at least generally reduces the potential of the orthodontic mechanical force module 14 from becoming disassembled (i.e., falling apart) while in the mouth of the patient.

Figure 5:
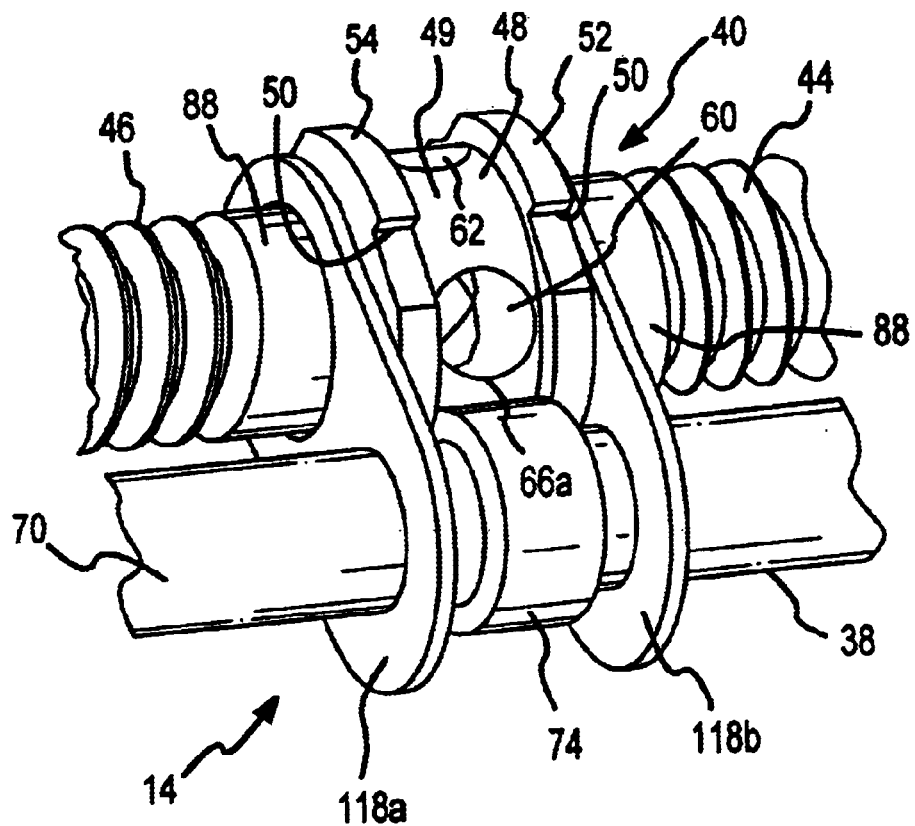
FIG. 5 is a perspective view of the orthodontic mechanical force module of FIG. 3, utilizing a pair of optional tangs.
Figure 6:
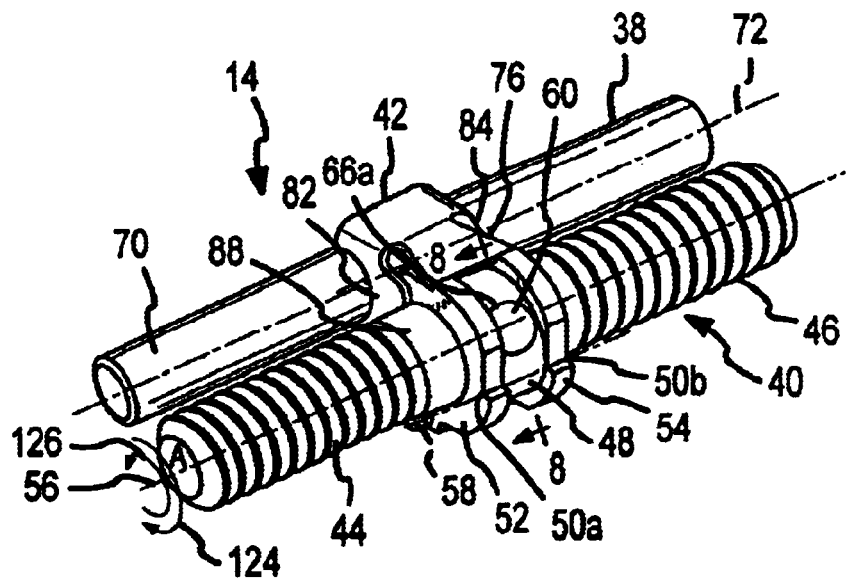
FIG. 6 is a perspective view of the spindle, the pawl assembly, and the guide pin assembly used by the orthodontic mechanical force module of FIG. 3, illustrating an engagement between a pawl and notches formed on an actuating head of the spindle.

Additional features may be utilized by the orthodontic mechanical force module 14 to reduce the potential for the same becoming disassembled while installed on a patient. FIG. 5 illustrates that at least one, and more preferably a pair of tangs 118a, 118b may be utilized to further reduce the potential of the force module 14 disassembling while in the mouth of patient. The tangs 118a, 118b are illustrated as oblong structures having separate apertures to enable both the spindle 40 and guide pin 70 to pass therethrough in a manner that does not restrict movement of the spindle 40 and guide pin 70 relative to the tangs 118a, 118b. The tangs 118a, 118b also at least assist in maintaining a desired spacing between the spindle 40 and the guide pin 70, and further in maintaining the same in the desired parallel relation. Other configurations may be appropriate for the tangs 118a, 118b to provide one or more of these functions. As shown in FIG. 5, at least portions of the actuating head 48 of the spindle 40 and the collar 74 of the guide pin 70 may be positioned between these tangs 118a, 118b as well.

Referring back to FIGS. 2–4 and 9, the first housing 36a includes an identification marker "A", and correspondingly, the first threaded section 44 of the spindle 40 also includes the same identification marker "A". Similarly, the second housing 36b has an identification marker "B", and the second threaded section 46 of the spindle 40 includes the same identification marker "B". It is important to note that the identification markers on the first threaded section 44 of the spindle 40 and the first housing 36a are different than the identification markers on the second threaded section 46 of the spindle 40 and second housing 36b. This is because these identification markers "A" and "B" are intended to at least generally assist in appropriate assembly of the orthodontic mechanical force module 14. In other words, these identification markers "A" and "B" at least potentially reduce trial and error in assembly of the orthodontic mechanical force module 14 (i.e., engaging the appropriate threaded section of the spindle 40 with the appropriate housing 36). While letters are utilized as identification markers in the illustrated embodiment(s), any appropriate identifier may be used (e.g., numbers, shapes, symbols, colors, and combinations thereof). Moreover, an arrow or the like may be included on each of the housings 36a, 36b to designate the direction of motion along the spindle 40 when increasing treatment forces.

Based upon the foregoing, it should be appreciated that the housings 36a, 36b move simultaneously along both the guide pin 70 and the spindle 40 in opposite directions. This movement may be used to apply at least generally opposing treatment forces on a patient. In this regard, each of the first and second housings 36a, 36b of the orthodontic mechanical force module 14 has an attachment area 98 where the wire segments 22a, 22b, respectively, of the palatal expansion device 11 are preferably affixed or anchored to the force module 14 in any appropriate manner (e.g., soldering, welding, brazing). End portions of the wire segments 22a would lay "lengthwise" within their corresponding attachment area 98 as illustrated in FIG. 2. Any appropriate way of interconnecting the housings 36a, 36b with an interconnecting structure between the force module 14 and the patient may be utilized as previously noted. The housings 36a, 36b may also be shaped to accommodate a desired/required interconnection.

As previously noted, the pawl assembly 42 cooperates with the actuating head 48 of the spindle 40 to control the angular or rotational position of the spindle 40, and thereby the positioning of the housings 36a, 36b along each of the length or length dimension of both the spindle 40 and the guide pin 70. Referring now to FIGS. 2–4, 6, and 10, the pawl assembly 42 of the orthodontic mechanical force module 14 is illustrated as being centrally located on the force module 14. This pawl assembly 42 includes at least one pawl 76 that is biased toward and into engagement with the peripheral surface of the flanges 52, 54 of the actuating head 48 of the spindle 40. Since the configuration of the pawl 76 in FIGS. 2–3 and 6 differs from that in FIGS. 4 and 10, the pawl 76 is identified by a "single prime" designation in FIGS. 4 and 10. Any appropriate way of biasing the pawl 76 toward the actuating head 48 of the spindle 40 may be utilized. For example, the pawl assembly 42 may be formed from an appropriate spring tempered metal or such that the pawl 76 is resiliently biased into engagement with the actuating head 48. Stated another way, the pawl 76 may have a certain amount of elasticity to provide the desired biasing force. In one embodiment, the pawl 76 is within a range of ¼ hard to full hard relative to the hardness range that a spring temper alloy material is able to demonstrate the capability of being hardened through induced work hardening. In another embodiment, the pawl 76 is within a range of about 160 KSI UTS to about 300 KSI UTS.

When the pawl 76 is biased against the periphery of the flanges 52, 54 of the actuating head 48 of the spindle 40 and during rotation of the spindle 40, the pawl 76 will follow the contour of these peripheral surfaces. When a notch 50 on each of the flanges 52, 54 is rotated into alignment with the pawl 76, the pawl 76 will snap into engagement with or become seated within each of these notches 50 due to the noted preferred resiliency of the pawl 76. This may make a "clicking" sound that may be used by the person making a force adjustment (e.g., a treatment protocol may provide for increasing the treatment force by a predetermined number of "clicks" each day until a return to the office of the practitioner for a checkup). If rotation of the spindle 40 is terminated at this time, the engagement of the pawl 76 within corresponding notches 50 on the flanges 52, 54 will preclude the spindle 40 from rotating in the opposite direction. Reciprocal forces being exerted on the force module 14 by the patient will further facilitate the seating of the pawl 76 against the aligned notches 50. For the application of the palatal expansion device 11, the engagement of the pawl 76 within the notches 50 allows for a rotation of the spindle 40 in a direction that moves the housings 36a, 36b simultaneously along both the guide pin 70 and the spindle 40 in a direction that increases an expansive force being exerted on those structures that are interconnected with the housings 36a, 36b. However, the engagement of the pawl 76 within the notches 50 will not allow for a rotation of the spindle 40 in a direction that moves the housings 36a, 36b relative to the spindle 40 in a direction that decreases an expansive force on those structures that are interconnected with the housings 36a, 36b. As such, the pawl assembly 42 in combination with the notches 50 addresses the tendency for the spindle 40 to back-off during orthodontic treatment applications.

As noted above, the pawl 76 preferably makes a "clicking" sound when being disposed in engagement with a notch 50 on each of the flanges 52, 54. Generally, the plurality of radially spaced notches 50 on the peripheral surface of each flange 52, 54 may be characterized as being separated by an arcuate surface. Each such arcuate surface may be characterized as a transition section. In one embodiment, each transition section is defined by a common radius that is located along the centerline of the spindle 40. The pawl 76 will then ride on a transition section on each flange 52, 54 when proceeding from one notch 50 to the next during rotation of the spindle 40 in a direction that provides for an increase in treatment forces. The notches 50 on each flange 52, 54 may be configured such that the pawl 76 will momentarily lose contact with the flanges 52, 54 when "dropping" into the next notch 50 on each flange 52, 54. This will generate the above-noted "clicking" sound. Although various configurations may allow the pawl 76 to momentarily lose contact to make such a "clicking" sound, in one embodiment each notch 50 on each flange 52, 54 is defined by a pair of at least generally flat surfaces that are disposed at least generally perpendicular to each other. Moreover, the flat surface of a given notch 50 that follows a transition section in the direction of rotation of the spindle 40 when increasing treatment forces may extend at least generally toward the centerline 56 of the spindle 40. This provides a "drop off" of sorts between this transition section and the other flat surface of the corresponding notch 50 onto which the pawl 76 "drops" to again preferably make a "clicking" sound.

The pawl assembly 42 desirably interfaces with both the spindle 40 and the guide pin 70 to provide the above-noted function(s). In this regard and referring to FIGS. 2–4, 6, and 10, the pawl assembly 42 has first and second arms 82, 84 that may be characterized as a mounting structure for the pawl assembly 42. Both of the flanges 52, 54 of the actuating head 48 of the spindle 40, as well as the medial portion 49 of the actuating head 48 of the spindle 40, are illustrated as being positioned between these first and second arms 82, 84 of the pawl assembly 42. Further, each of these arms 82, 84 of the pawl assembly 42 generally has a first concave recess 86 complementary in configuration to (i.e., capable of cooperatively interfacing with) the smooth cylindrical sections 88. Similarly, the first and second arms 82, 84 each have a second concave recess 90 complementary in configuration to the guide pin 70 of the guide pin assembly 38. These recesses 86, 90 are on opposite sides of the pawl assembly 42 and at least generally project in opposite directions. It may be said then that one or both of these recesses 86, 90 enable the pawl assembly 42 to "straddle" a portion of the generally smooth, arcuate surfaces of one or both of the guide pin 70 and the lateral portions 88 of the actuating head 48 of the spindle 40. That is, these recesses 86, 90 enable a portion of the pawl assembly 42 to be interposed or "sandwiched" between the guide pin 70 and the spindle 40. Accordingly, the arms 82, 84, as well as the concave recesses 86, 90 found therein, at least reduce the potential of the pawl assembly 42 from being undesirably disassociated from the orthodontic mechanical force module 14. A small amount (e.g., 0.002 inch) of clearance between the pawl assembly 42 and one or both the guide pin assembly 38 and the spindle 40 may be appropriate to enable the spindle 40 to be rotated unencumbered by any significant frictional force generated by the interface of the pawl assembly 42 with the spindle 40.

The pawl assembly 42 and the actuating head 48 (via the flanges 52, 54) of the spindle 40 may be referred to, in combination, as a ratchet. "Ratchet," or "ratcheting," generally refers to the ability to turn, rotate, and/or torque a first component (e.g., the spindle 40) of the orthodontic mechanical force module 14 to move or permit motion of the first component in substantially only a first direction 124 (FIG. 6) due to an interfacing relationship with a second component (e.g., the pawl assembly 42) of the force module 14. This interfacing relationship includes direct physical contact between the spindle 40 and the pawl 76 of the pawl assembly 42 and is referred to herein as an "activated" position of the pawl assembly 42. This may also be characterized as the module 40 being operable in a first mode to provide a greater resistance to rotation of the spindle 40 in one direction versus the other. Conversely, taking the pawl 76 out of direct physical contact with the spindle 40, and more specifically out of engagement with the notches 50 formed on peripheral surfaces of the flanges 52, 54, enables the spindle 40 to rotate in a second direction 126 (FIG. 6) opposite the first direction 124. This may also be characterized as the module 40 being operable in a second mode to provide at least substantially the same magnitude of resistance (including no substantial resistance at all) to rotation of the spindle 40, regardless of the direction of rotation. This is referred to herein as a "deactivated" position of the pawl assembly 42. Since the pawl 76 is biased in the direction of the actuating head 48 of the spindle 40, the pawl 76 needs to be forced out of engagement with the actuating head 48 by an amount so as to sufficiently clear the peripheral surfaces of the flanges 52, 54 on which the notches 50 are formed.

Figures 11, 12:
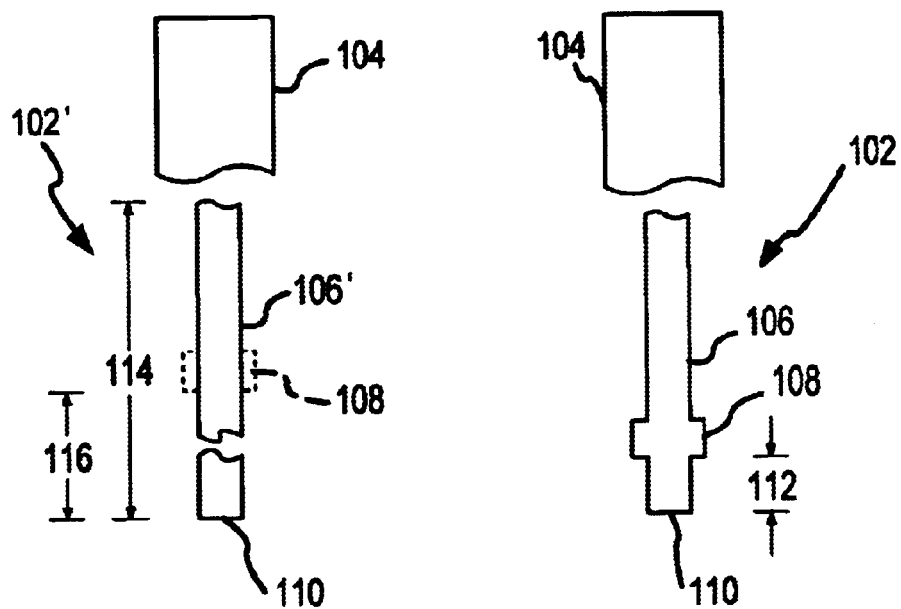
FIG. 11 is a plan view of one embodiment of an adjustment tool for the orthodontic mechanical force module assembly of FIGS. 3 and 13.
FIG. 12 is a plan view of another embodiment of an adjustment tool for the orthodontic mechanical force module of FIGS. 3 and 13.
Figure 9:
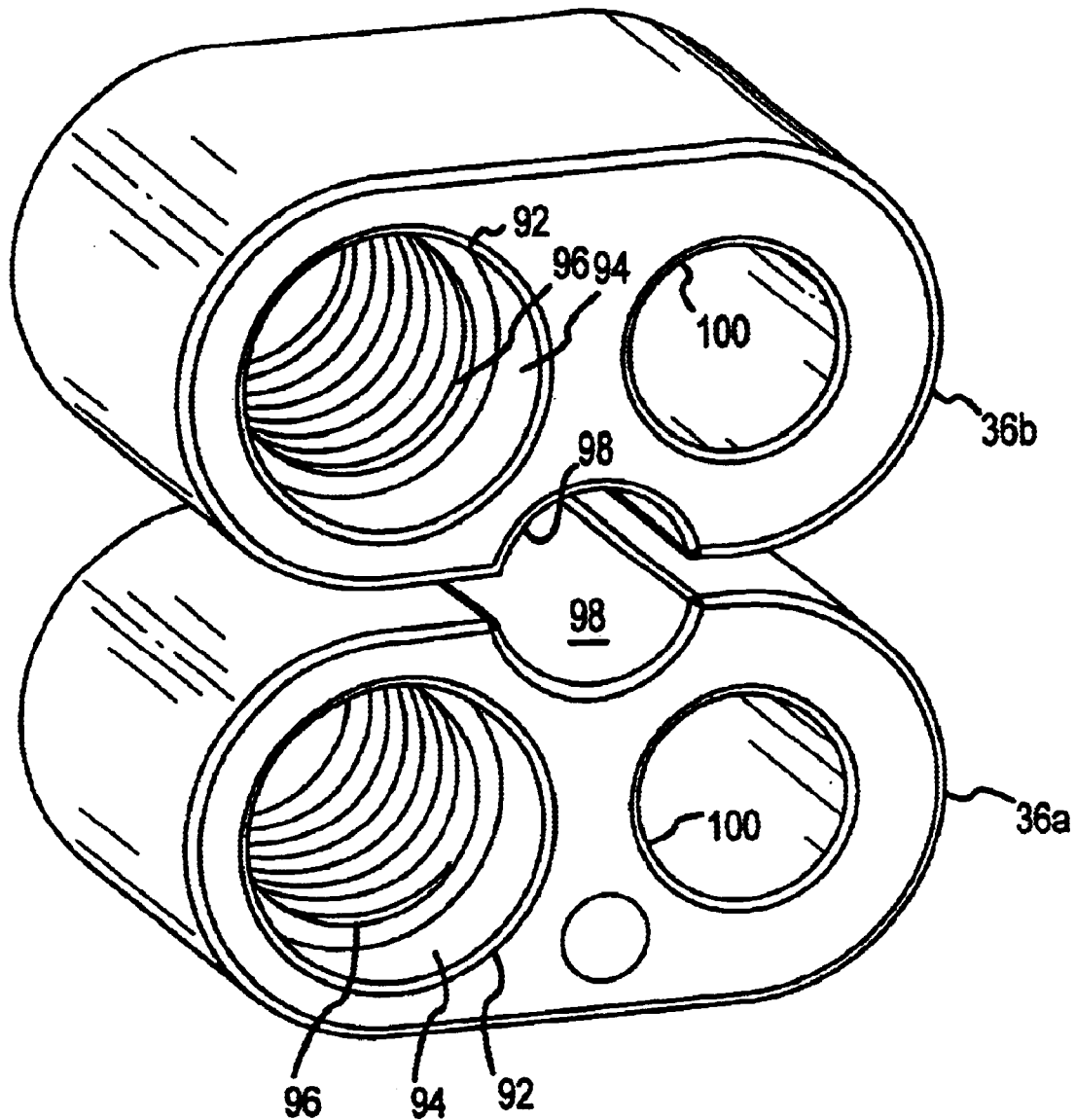
FIG. 9 is a perspective view of the housings used by the orthodontic mechanical force module of FIG. 3.
Figure 13:
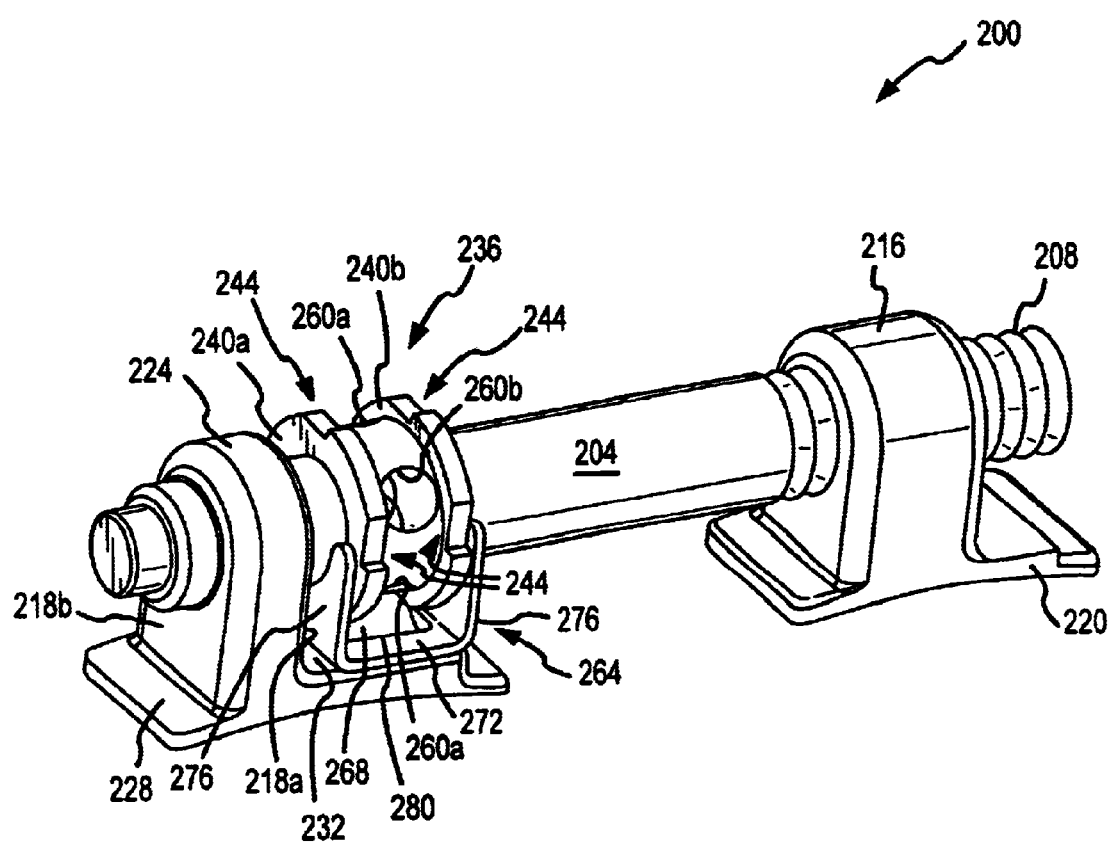
FIG. 13 is a perspective view of another embodiment of an orthodontic mechanical force module.
Figure 14:
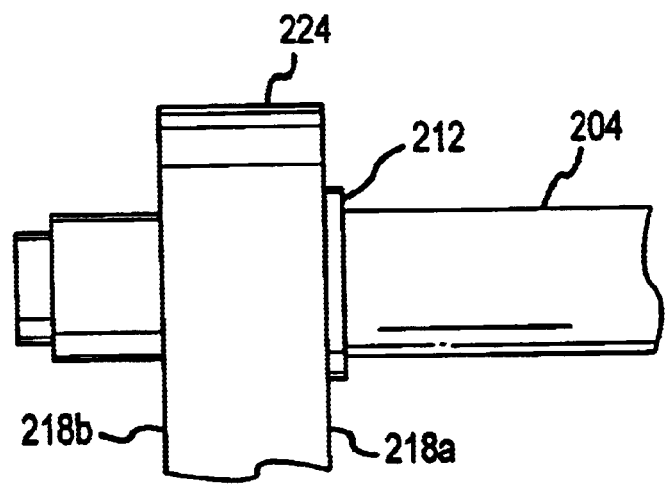
FIG. 14 is a side view of a portion of the spindle and the housing that is only rotatably interconnected with the spindle from the orthodontic force module of FIG. 13.
Figure 15:
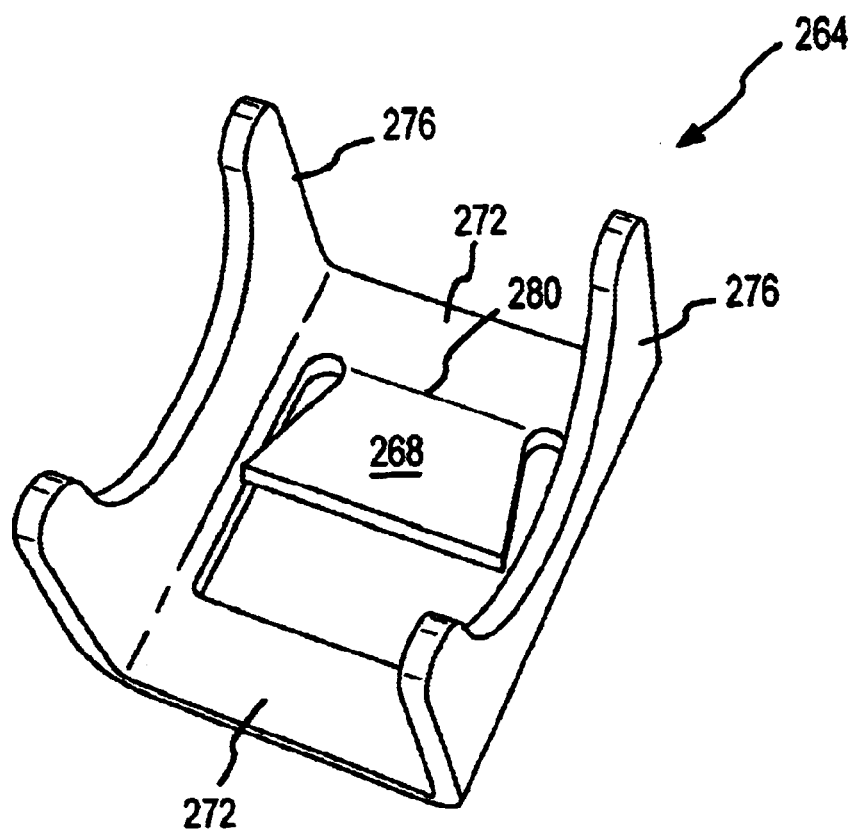
FIG. 15 is a perspective view of the pawl assembly used by the orthodontic force module of FIG. 13.

FIGS. 11–12 illustrate first and second adjustment tools 102, 102', respectively, for engagement with either of the adjustment holes 60, 62 of the spindle 40 (as well as for use with the orthodontic mechanical force module 200 to be described below). Each of the adjustment tools 102, 102' has a handle 104 and a shaft 106, 106' that is insertable into (or at least generally engageable with) the adjustment holes 60, 62 of the spindle 40. Referring specifically to the adjustment tool 102 of FIG. 11, the shaft 106 is equipped with an annular stop feature 108 that is located toward an engagement end 110 of the shaft 106 to limit an extent of possible insertion of the shaft 106 within an adjustment hole 60, 62 of the spindle 40. That is, a distance 112 between the engagement end 110 of the tool 102 and the stop feature 108 of the tool 102 is less than the distance 51 (FIG. 8) of the adjustment holes 60, 62. Thus, the shaft 106 of the adjustment tool 102 cannot pass through the entirety of either of the adjustment holes 60, 62. As such, the adjustment tool 102 is unable to extend beyond the particular through hole 62, 64, is thereby unable to engage a portion of the pawl 76 that is disposed in overlying and spaced relation thereto, and is thereby unable to move the pawl 76 of the pawl assembly 42 sufficiently out of engagement with the notches 50 on the flanges 52, 54 of the actuating head 48 of the spindle 40. As such, the adjustment tool 102 may only be used to increase the magnitude of the treatment force for the illustrated palatal expansion application, and not to decrease the magnitude of the treatment force. This adjustment tool 102 may be of any appropriate configuration. Stated another way, the adjustment tool 102 may be used to rotate the spindle 40 in only one direction.

FIG. 12 illustrates another adjustment tool 102' that is also designed for engagement with any of the adjustment holes 60, 62 of the spindle 40. This adjustment tool 102' differs from the adjustment tool 102 of FIG. 11 in that the shaft 106' of the adjustment tool 102' is designed to allow a user to extend the same through an entirety of a desired adjustment hole 60, 62 of the spindle 40. Accordingly, a length 114 of the shaft 106' is generally long enough to enable the user the pass the same through an entirety of a particular adjustment hole 60, 62 so that the engagement end 110 of the shaft 106' may be biased against the pawl assembly 42 to disengage the pawl 76 from physical contact with the spindle 40 or to at least sufficiently "unseat" the pawl 76 from the corresponding notches 50 on the flanges 52, 54. The adjustment tool 102' may also be equipped with an optional stop feature 108. However, a distance 116 between this optional stop feature 108 and the engagement end 110 of the shaft 106' is generally great enough to enable the user the pass the same through an entirety of a particular adjustment hole 60, 62 so that the engagement end 110 of the shaft 106' may be biased against the pawl assembly 42 to disengage the pawl 76 from physical contact with the spindle 40. Accordingly, this is a type of adjustment tool 102' that may be preferred to be reserved for use by an orthodontic professional since both tightening and loosening operations may be achieved using the same. That is, the tool 102' may be used to rotate the spindle 40 in either direction. An example of an appropriate adjustment tool for a palatal expansion application is described in U.S. Pat. No. 5,133,659, which is incorporated by reference herein in its entirety, and which may be adapted in accordance with the foregoing discussion regarding FIGS. 11 and 12 for use in combination with the orthodontic mechanical force module 14 or 200.

It may be desirable to move the housings 36a, 36b along the spindle 40 in a direction that corresponds with a reduction of treatment forces using the adjustment tool 102' for any number of reasons. For instance, more than the desired incremental increase in treatment forces may have been applied to the patient (via an over-rotation of the spindle 40 or an overactivation of the force module 14). Patient discomfort may also need to be addressed at times. Some orthodontic practitioners may want to apply enhanced treatment forces for a certain amount of time, followed by a "rest period" where the treatment forces are reduced, possibly to a significant extent or even possibly eliminated. Finally and prior to the initial installation of the force module 14, there may have been some regression or relapse by the patient. That is, the force module 14 (and possibly other components) will typically be fabricated from a stone model of the relevant dental arch. From the time that the stone model is made and the time that the module 14 is fabricated and installed, the patient's dental arch may have changed. Each of these situations may be addressed through use of the adjustment tool 102' to move the housings 36a, 36b along the spindle 40 in a direction that is opposite to that associated with the intended treatment forces.

Generally, when the pawl assembly 42 is in an activated position, a spacing between the first and second housings 36a, 36b of the orthodontic mechanical force module 14 is adjusted by initially inserting the shaft 106 of an appropriate adjustment tool (e.g., 102/102') into an appropriate adjustment hole 60, 62 in the spindle 40. As noted above, one end of either the adjustment hole 60 or the adjustment hole 62 will be disposed at the same position for engagement by the adjustment tool 102/102' due to the clocking of the adjustment holes 60, 62 and the notches 50, regardless of which pair of notches 50 on the bosses 52, 54 is being engaged by the pawl assembly 42 to restrict rotation of the spindle 40 in an undesired direction. Since adjustments will typically be made on a relatively frequent basis when using the force module 14, this self-locating feature provides significant advantages. Subsequently, the spindle 40 is rotated by rotationally urging (i.e., torquing) the handle 104 of the adjustment tool 102 (or the tool 102') to rotate the spindle 40 in the first direction 124. Accordingly, the pawl 76 of the pawl assembly 42 "clicks into" or engages a desired notch 50 on each of the flanges 52, 54 of the actuating head 48 to substantially prevent rotational movement of the spindle 40 in the second direction 126. As also noted above, once the adjustment tool 102/102' has been inserted into an end of a particular adjustment hole 60, 62, the adjustment tool 102/102' may be rotated 90 degrees for engagement by the pawl assembly 42 with the next set of notches 50 on the bosses 52, 54 without encountering any obstruction from the module 14, again due to the clocking of the adjustment holes 60, 62 and the notches 50. The adjustment tool 102/102' is then removed from the adjustment hole 60, 62 without encountering any obstruction from the module 14, again due to the clocking of the adjustment holes 60, 62 and the notches 50. Engagement of the pawl 76 with a notch 50 on each of the flanges 52, 54 of the actuating head 48 beneficially prevents undesired "back rotation" of the spindle 40 once the desired/required adjustment has been made. Since the notches 50 are preferably equidistantly spaced about the peripheral surfaces of the flanges 52, 54 of the actuating head 48, substantially precise, defined, incremental adjustment of the orthodontic mechanical force module 14 can be obtained.

To disengage the pawl 76 of the pawl assembly 42 (i.e., to deactivate the pawl assembly 42), the adjustment tool 102' may be extended through an entirety of an appropriate adjustment hole 60, 62 and biased against the pawl assembly 42 to take the pawl 76 out of direct physical contact with the actuating head 48, thus enabling the spindle 40 to rotate in the second direction 126. In other words, taking the pawl 76 out of direct physical contact with the actuating head 48 removes the inhibition of rotation of the spindle 40 in the second direction 126.

The above-described orthodontic mechanical force module 14 may be assembled using one or more appropriately configured fixtures or in any appropriate manner. The module 14 may be disassembled in this same general manner as well. The spindle 40, guide pin 70, and the pawl assembly 42 may be disposed within at least generally concave areas formed in a first fixture to locate the same in the desired relative position for the orthodontic mechanical force module 14. After having attached the wire segments 22a, 22b to the housings 36a, 36b, respectively, the housings 36a, 36b may be disposed such that the ends 80 of the spindle 40 are introduced into the non-threaded portions 94 of the adjustment bore 92 and so as to abut the threaded portion 96 of each housing 36a, 36b, and further such that the ends of the guide pin 70 are disposed within the guide bore 100 of each of the housings 36a, 36b. The orthodontic mechanical force module 14 in this form may then be removed from this first fixture by holding onto the wire segments 22a, 22b, and may then be disposed within a base of a second fixture having a pair of v-shaped grooves that are formed on an upper surface of a pair laterally spaced and vertically recessed legs. The wire segments 22a, 22b may be disposed in these v-shaped grooves and the housings 36a, 36b will then interface with the upper surface of these laterally spaced and vertically recessed legs of the base of the second fixture. The actuating head 48 of the spindle 40 and the pawl assembly 40 are then suspended between the two laterally spaced legs of the base of the second fixture. The pair of laterally spaced legs of an at least generally u-shaped clamp plate (in plan view) of the second fixture is then disposed on the upwardly facing surface of the housings 36a, 36b, and then is appropriately secured to the base of the second fixture (e.g., using one or more set screws), all while grasping the housings 36a, 36 and pulling the same inwardly toward each other. The actuating head 48 of the spindle 40 and the pawl assembly 42 are thereby disposed in the space between the legs of the clamp plate and the recessed legs of the base. The housings 36a, 36b are thereby vertically restrained, but are not clamped between the clamp plate and base of the second fixture. As such, the housings 36a, 36b are able to slide relative to the legs of both the clamp plate and the base of the second fixture when threading the housings 36a, 36b onto the spindle 40. In this regard, an appropriately shaped pry pin or the like (which may be disposed within a slot formed in the base of the second fixture) is extended out to engage the underside of the pawl 76 of the pawl assembly 42 to move the same at least generally away from the spindle 40 and to dispose and retain the pawl 42 in sufficiently spaced relation to the notches 50 on the flanges 52, 54 so that the spindle 40 may be rotated in either direction. This pry pin may then be appropriately fixed in this position. The tool 102/102' may then be used to start to thread the spindle 40 into each of the housings 36a, 36b by rotating the spindle 40 in a direction that draws the housings 36a, 36b toward each other. Once a sufficient threaded engagement has been established, a screwdriver may be used to continue to rotate the spindle 40 (via engagement with the slot 78 on one of the ends 80 of the spindle 40, as illustrated in FIG. 7) in a direction that draws the housings 36a, 36b toward each other by simultaneously moving along both the spindle 40 and the first guide pin 70, typically to the position illustrated in FIG. 4.

Another embodiment of an orthodontic mechanical force module is presented in FIGS. 13–16 and is identified by reference numeral 200. The orthodontic mechanical force module 200 is particularly suited for molar distalization, although the same may be utilized for any suitable orthodontic application, including to generate/apply a contractive or expansive force to the patient. The orthodontic mechanical force module 200 generally includes a spindle 204 that is rotatably supported by both a first housing 216 and a second housing 224. These housings 216 and 224 are spaced along a length dimension of the spindle 204. Changing the spacing between the housings 216 and 224 along the spindle 204 generates and applies a-treatment force to a patient on which the orthodontic mechanical force module 200 is installed. Both the first housing 220 and the second housing 224 include a mounting base (220 and 228, respectively) that are appropriately contoured to interface with a tooth. In a molar distalization application, the mounting bases 220 and 220 would typically be installed (e.g., via an appropriate bonding adhesive or cement) on different teeth on the buccal of one side of the patient's dental arch. However, any way of installing the module 204 on the patient may be utilized.

As noted, changing the spacing between the first housing 216 and the second housing 224 generates and applies the treatment force to the patient. In this regard, the spindle 204 includes a threaded section 208 that interfaces with the first housing 216. Threads (not shown) are disposed on a wall of a bore through the first housing 216 and through which the spindle 204 extends. This thereby not only rotatably interconnects the first housing 216 with the spindle 204, but establishes a threaded interconnection as well. Rotation of the spindle 204 moves the first housing 216 along the length of the spindle 204 because of the corresponding threaded interconnection.

The second housing 224 in the case of the orthodontic mechanical force module 200 rotatably supports the spindle 204, but does not move along the length dimension of the spindle 204 during rotation of the spindle 204. Instead, the second housing 224 functions as an anchor of sorts for the treatment forces generated by moving the first housing 216 along the length dimension of the spindle 204 in the desired direction to generate the desired type of treatment force (e.g., to open or close a space in the patient's dental arch). In this regard, a typically smooth cylindrical bore extends through the first housing 224 to receive and rotatably support the spindle 204. A stop 212 (FIG. 14) having a larger diameter than this bore is mounted on or is part of the spindle 204 (so as to have a fixed position along a length dimension of the spindle 204) and abuts a side 218a of the housing 224 for the case where expansive forces are to be generated by the orthodontic mechanical force module 200. Expansive forces would be generated by moving the first housing 216 away from the second housing 224 to generate the desired treatment forces. The stop 212 would have to be mounted on or part of the spindle 204 to abut the side 218b in the event the orthodontic mechanical force module 200 was used to generate a contractive force (by a movement of the first housing 216 toward the second housing 224).

Rotation of the spindle 204 is controlled in the same general manner discussed above in relation to the orthodontic mechanical force module 14. An actuating head 236 is mounted on and rotates with the spindle 204, and has the attributes discussed above in relation to the orthodontic mechanical force module 14. This actuating head 236 includes a pair of flanges or bosses 240a, 240b that are spaced along the length of the spindle 204. A plurality of notches 244 are formed on a peripheral surface 242 of these bosses 240a, 240b and are radially spaced. As in the case of the orthodontic mechanical force module 14, preferably the same spacing is used between each adjacent pair of notches 244 on each boss 240a, 240b (i.e., preferably the notches 244 on each boss 240a, 240 are equally radially spaced) and each notch 244 on the boss 240a is properly aligned with a notch 244 on the boss 240b. The bosses 240a, 240b with these notches 244 function as a ratchet wheel to control how the spindle 204 may be rotated. Other ratchet wheel configurations could be utilized, although the illustrated configuration is beneficial in one or more respects.

Adjacent notches 244 on the peripheral surface 242 of each boss 240a, 240b are separated by a transition surface 256. In the illustrated embodiment, each transition surface 256 is defined by a common radius from a common center (FIG. 16, and corresponding with a centerline 206 of the spindle 204, as well as the actuating head 236), although such need not be the case. Each notch 244 is defined by a first face 248 and a second face 252. Both faces 248 and 252 are at least generally flat or planar surfaces in the illustrated embodiment and are disposed in at least generally perpendicular relation to each other. The first face 248 of each notch 244 is disposed at least generally perpendicular to the adjacent transition surface 256. Stated another way, the first face 248 of each notch 244 extends at least generally toward the center 206. Other configurations for the notches 244 may be appropriate.

The orthodontic mechanical force module 200 further includes a pawl assembly 264 that is functionally similar to that discussed above in relation to the orthodontic mechanical force module 14. Components of the pawl assembly 264 includes a base 272, a pawl 268, and a pair of spindle guides 276. The base 272 is disposed on a support 232 of the mounting base 228 of the second housing 224. The pawl 268 extends upwardly from the base 272 from location 280 at an appropriate angle and is simultaneously engageable with both bosses 240a, 240b on the spindle 204 to control rotation of the spindle 204. The pair of spindle guides 276 extend upwardly from the base 272 and cradle at least a portion of the spindle 204 for locating the pawl assembly 264.

Figure 16:
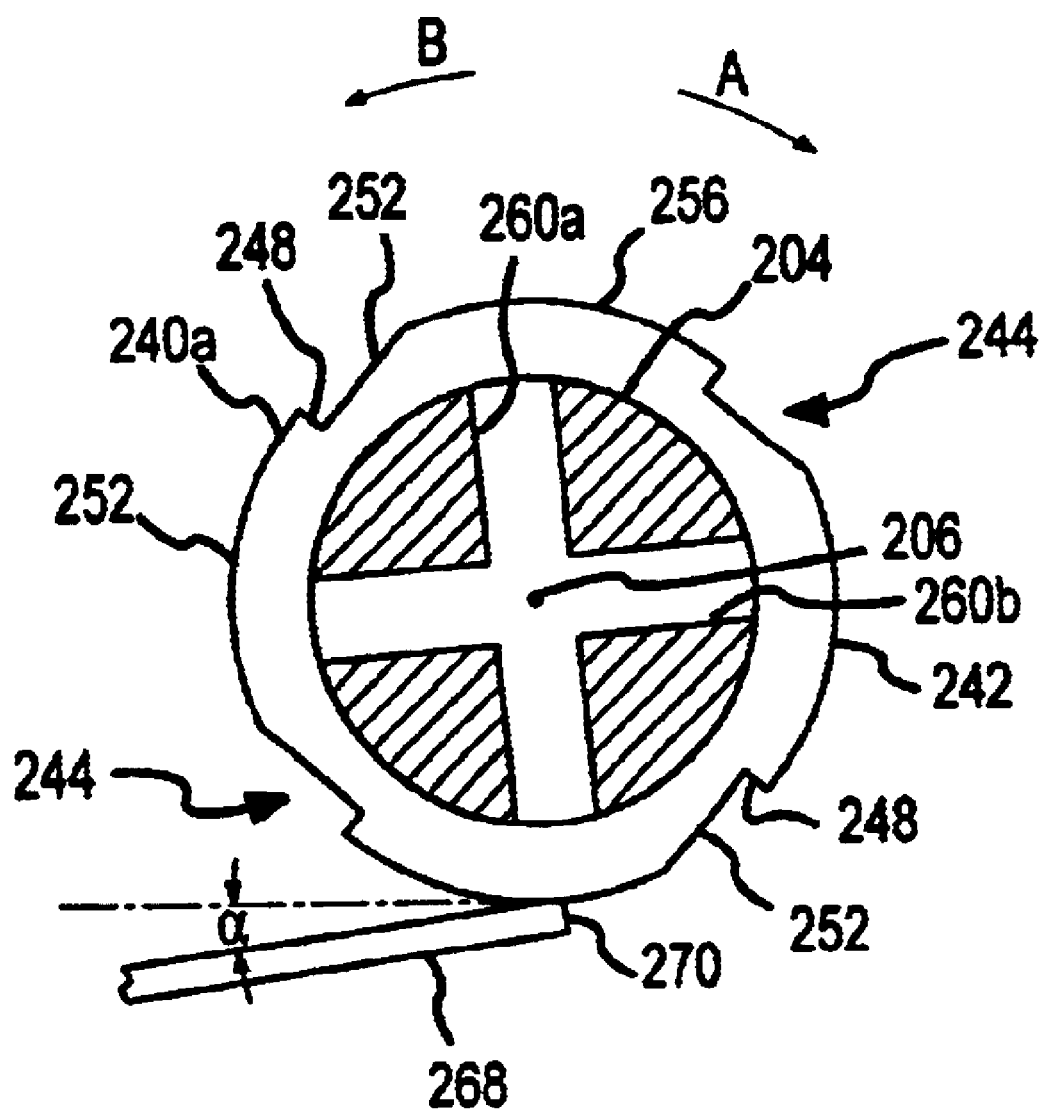
FIG. 16 is a cross-sectional view taken through the adjustment holes on the spindle of the orthodontic mechanical force module of FIG. 13.

Engagement of a free end 270 of the pawl 268 against the first face 248 of any of the notches 244 will prevent further rotation of the spindle 204 and actuating head 236 in the direction of the arrow A in FIG. 16. This would be a direction that would tend to reduce the magnitude of the treatment forces being exerted on the patient by the module 200. However, the spindle 204 and actuating head 236 may be rotated in the direction of the arrow B illustrated in FIG. 16 any desired/required amount to increase the magnitude of the treatment forces being exerted on the patient by the module 200. Preferably, the pawl 268, due to the mechanical properties of the spring-temper material from which it formed, is biased toward the peripheral surface 242 of both bosses 240a, 240b so as to make a snapping or clicking sound when proceeding from a transition surfaces 256 into a notch 244 on both of the bosses 240a, 240b.

Application of treatment forces by the orthodontic mechanical force module 200 are opposed by the teeth of the patient on which the module 200 is installed or anchored. These opposing forces will attempt to rotate the spindle 204 and actuating head 236 in the direction indicated by the arrow A in FIG. 16 as treatment forces are increased. However, with the end 270 of the pawl 268 being in engagement with the first face 248 of a notch 244 on each of the bosses 240a, 240b, the spindle 204 and actuating head 236 are not able to rotate in the direction of the arrow A, absent some type of failure of the pawl 268. Preferably, the pawl 268 is disposed relative to the bosses 240a, 240 so as to be in at least substantially direct mechanical opposition to a rotation of the spindle 204 and actuating head 236 when engaged with a first face 248 of a pair of notches 244 on the bosses 240a, 240b. In one embodiment, the pawl 268 is disposed at an angle α that is within a range of about +/−20 degrees relative to any tangent 284 to any of the transition surfaces 256. Stated another way, the pawl 268 is disposed at an angle from about 70 degrees to about 110° relative to a radial line extending from the centerline 206 to the location where the pawl 268 is engaging the peripheral surface 242 of either the boss 240a or 240b.

Rotation of the spindle 204 and actuating head 236 when the orthodontic mechanical force module 200 is installed on a patient is accomplished through a pair of adjustment holes 260a, 260b. These adjustment holes 260a, 260b extend through the spindle 204 at a location that is between the bosses 240a, 240b in the illustrated embodiment. Preferably, these adjustment holes 260a, 260b are disposed perpendicularly to each other and intersect at the centerline 206 of the spindle 204/actuating head 236. As in the case of the orthodontic mechanical force module 14 described above, preferably the adjustment holes 260a, 260b are clocked relative to the notches 244 on the bosses 240a, 240b such that one end of either of the adjustment hole 260a, 260b will be disposed at the same position for engagement by either of the adjustment tools 102, 102', regardless of which pair of notches 244 on the bosses 240a, 240b is being engaged by the pawl 268, and further will be disposed so as to allow for 90 degrees of rotation of the actuating head 236 and spindle 204 without encountering any obstruction by the module 200 during this rotation and during any subsequent removal of the tool 102/102' that was used to make the adjustment.

The pawl 268 preferably makes a "clicking" sound when being disposed in engagement with a notch 244 on each of the bosses 240a, 240b. Generally, the plurality of radially spaced notches 244 on the peripheral surface 242 of each 240a, 240b may be characterized as being separated by an arcuate transition surface 256 as noted above. In one embodiment, each transition surface 256 is defined by a common radius that is located along the centerline 206 of the spindle 204 as also noted above. The pawl 268 will then ride on a transition surface on each boss 240a, 240b when proceeding from one notch 244 to the next during rotation of the spindle 204 in a direction that provides for an increase in treatment forces (arrow B in FIG. 16). The notches 244 on each boss 240a, 240b may be configured such that the pawl 268 will momentarily lose contact with the bosses 240a, 240b when "dropping" into the next notch 244 on each boss 240a, 240b. This will generate the above-noted "clicking" sound. Although various configurations may allow the pawl 268 to momentarily lose contact to make such a "clicking" sound, in one embodiment each notch 244 on each boss 240a, 240b again is defined by a pair of at least generally flat surfaces (first face 248 and second face 252) that may be disposed at least generally perpendicular to each other. Moreover, the first face 248 of a given notch 244 that follows a transition surface 256 in the direction of rotation of the spindle 204 when increasing treatment forces (arrow B in FIG. 16) may extend at least generally toward the centerline 206 of the spindle 204. This provides a "drop off" of sorts between this transition surface 256 and the second face 252 of the corresponding notch 244 onto which the pawl 268 "drops" to again preferably make a "clicking" sound. That is, the pawl 268 may proceed directly from a transition surface 256 to the second face 252 of a given notch 244 without contacting the first face 248 of this same notch 244.

It should be appreciated that even when the pawl 268 is engaged with the peripheral surface 242 of each of the bosses 240a, 240b, it may be possible for the spindle 204 to be rotated in a direction associated with a reduction of treatment forces, but only by a-distance that is less than the distance between adjacent notches 244. That is, when proceeding from one notch 244 on each of the bosses 240a, 240 to the next notch as the spindle 204 is rotated in the direction of the arrow B in FIG. 16 (to increase treatment forces), rotation of the spindle 204 may be stopped prior to having the pawl 268 seat in the next notch 244 on each boss 240a, 240. The spindle 204 could then be rotated back in the direction of the arrow A (to decrease the treatment forces), but only back to the notch 244 on each of the bosses 240a, 240b that was engaged by the pawl 268 prior to initiating rotation of the spindle 204. This would similarly apply to the orthodontic mechanical force module 14 as well.

One difference between the orthodontic mechanical force module 200 and the module 14 is the lack of any guide pin. However the module 200 could be adapted to include one or more guide pins. Another difference between the modules 200 and 14 is that only one housing moves along the spindle during rotation in the case of the module 200, while both housings move along the spindle in the case of the module 14. However, the module 200 could be adapted to have both of its housings move along the spindle during rotation as well. The various features discussed in relation to the module 14 may be utilized by the module 200, and vice versa.

The foregoing description of the present invention has been presented for purposes of illustration and description. Furthermore, the description is not intended to limit the present invention to the form disclosed herein. Consequently, variations and modifications commensurate with the above teachings, and skill and knowledge of the relevant art, are within the scope of the present invention. The embodiments described hereinabove are further intended to explain best modes known of practicing the present invention and to enable others skilled in the art to utilize the present invention in such, or other embodiments and with various modifications required by the particular application(s) or use(s) of the present invention. It is intended that the appended claims be construed to include alternative embodiments to the extent permitted by the prior art.

What is claimed:

1. An orthodontic mechanical force module, comprising:
   first and second housings;
   a spindle that extends within and is rotatable relative to each of said first and second housings, wherein said first housing is further threadably interconnected with said spindle to move said first housing along a length dimension of said spindle by a rotation of said spindle to change a spacing between said first and second housings in a dimension measured along said length dimension of said spindle; and
   a unidirectional ratchet associated with said spindle, wherein said unidirectional ratchet controls rotation of said spindle, wherein said unidirectional ratchet comprises a ratchet wheel and a pawl, wherein said spindle comprises said ratchet wheel such that said ratchet wheel rotates along with a remainder of said spindle, wherein said pawl is at least engageable with said ratchet wheel, wherein said spindle comprises a first through hole, and wherein said pawl is disposed in at least partially overlying and spaced relation to an adjacent end of said first through hole.

2. An orthodontic mechanical force module, as claimed in claim 1, wherein:
   said second housing remains at a constant position along said length dimension of said spindle during said rotation of said spindle.

3. An orthodontic mechanical force module, as claimed in claim 1, wherein:
   said second housing is further threadably interconnected with said spindle to also move said second housing along said length dimension of said spindle during said rotation of said spindle, wherein said first and second housings move simultaneously in opposite directions along said length dimension of said spindle during said rotation of said spindle.

4. An orthodontic mechanical force module, as claimed in claim 1, wherein:

said pawl is resiliently biased into engagement with said ratchet wheel.

5. An orthodontic mechanical force module, as claimed in claim 4, wherein:

said pawl comprises a spring temper metal.

6. An orthodontic mechanical force module, comprising:

first and second housings;

a spindle that extends within and is rotatable relative to each of said first and second housings, wherein said first housing is further threadably interconnected with said spindle to move said first housing along a length dimension of said spindle by a rotation of said spindle to change a spacing between said first and second housings in a dimension measured along said length dimension of said spindle;

first means for allowing only unidirectional rotation of said spindle in a first direction to change a spacing between said first and second housings along said length dimension of said spindle by a movement of at least said first housing along said length dimension of said spindle, wherein said first means comprises a unidirectional ratchet wheel and a pawl, wherein said spindle comprises said ratchet wheel such that said ratchet wheel rotates along with a remainder of said spindle, wherein said pawl is at least engageable with said ratchet wheel, wherein said spindle comprises a first through hole, and wherein said pawl is disposed in at least partially overlying and spaced relation to an adjacent end of at least part of said first through hole; and second means for deactivating said first means to allow bidirectional rotation of said spindle, wherein said second means comprises said first through hole.

7. An orthodontic mechanical force module, as claimed in claim 6, wherein:

said pawl is biased into engagement against said ratchet wheel.

8. An orthodontic mechanical force module, as claimed in claim 6, wherein:

said pawl is resiliently biased against said ratchet wheel.

9. An orthodontic mechanical force module, comprising:

first and second housings;

a spindle that extends within and is rotatable relative to each of said first and second housings, wherein at least one of said first and second housings is threadably interconnected with said spindle to move said at least one of said first and second housings along a length dimension of said spindle during a rotation of said spindle to change a spacing between said first and second housings in a dimension measured along said length dimension of said spindle;

a plurality of detent apertures that are associated with said spindle, that are radially spaced about an axis along which said length dimension of said spindle extends, and that rotate along with said spindle;

a detent engageable with each of said plurality of detent apertures, wherein engagement of said detent with any of said plurality of detent apertures prevents rotation of said spindle in a first direction;

a plurality of adjustment apertures that extend at least within said spindle and that are radially spaced about said axis along which said length dimension of said spindle extends, wherein all of said plurality of adjustment apertures are located within a first region that extends completely about an entire circumference of said spindle and that extends along only a portion of said length of said spindle, wherein none of said plurality of detent apertures are located in said first region of said spindle; and a ratchet wheel associated and rotatable with said spindle and a pawl that is at least engageable with said ratchet wheel to prevent rotation of said ratchet wheel, and thereby said spindle, in said first direction, wherein said ratchet wheel comprises said plurality of detent apertures, wherein said pawl comprises said detent, wherein said ratchet wheel comprises first and second bosses that are spaced along said length dimension of said spindle and a plurality of notches disposed on a peripheral surface of each of said first and second bosses, wherein said plurality of notches comprises said plurality of detent apertures, and wherein said pawl is at least simultaneously engageable with one of said plurality of notches on each of said first and second bosses.

10. An orthodontic mechanical force module, as claimed in claim 9, wherein:

said plurality of adjustment apertures are disposed between said first and second bosses.

11. An orthodontic mechanical force module, as claimed in claim 9, wherein:

said pawl is biased against said ratchet wheel and is disposed in overlying and spaced relation to at least part of at least one of said adjustment apertures when said pawl prevents rotation of said ratchet wheel in said first direction.

12. An orthodontic mechanical force module, as claimed in claim 9, wherein:

said pawl is disposed in at least substantially direct mechanical opposition to a rotation of said ratchet wheel in said first direction.

13. An orthodontic mechanical force module, as claimed in claim 9, wherein:

said plurality of adjustment apertures consist of first and second through holes that are disposed in perpendicular relation to each other and that extend entirely through said spindle.

14. An orthodontic mechanical force module, as claimed in claim 9, wherein:

said plurality of detent apertures and said plurality of adjustment apertures are clocked such that one of said plurality of adjustment apertures is presented at the same position for a rotational adjustment of said spindle, by insertion of an adjustment tool therein, each time said detent is in engagement with at least one of said plurality of detent apertures, and further such that said spindle may then be rotated at least 90° without encountering any obstruction by said orthodontic mechanical force module.

15. An orthodontic mechanical force module, as claimed an claim 14, wherein:

said plurality of detent apertures consist of at least one set of four detent apertures spaced every 90 degrees about said axis and disposed at a common longitudinal position along said length dimension of said spindle.

16. A method of operating an orthodontic mechanical force module installed on a patient, said method comprising the steps of:

increasing a magnitude of a treatment force being exerted on the patient by said orthodontic mechanical force module, said increasing step comprising engaging said orthodontic mechanical force module with a first tool; and decreasing said magnitude of said treatment force being exerted on the patient by said orthodontic mechanical force module, said decreasing step comprising engaging said orthodontic mechanical force module with a second tool that is of a different configuration than said first tool.

17. A method as claimed in claim 16, wherein:
said increasing step comprises changing a spacing between first and second housings along a spindle in a first manner, said wherein said decreasing step comprises changing a spacing between said first and second housings along said spindle in a second manner that is opposite said first manner.

18. A method, as claimed in claim 16, wherein said first tool is unable to execute said decreasing step.

19. A method of operating an orthodontic mechanical force module installed on a patient, said method comprising the steps of:
executing a first changing step comprising changing a spacing between first and second housings of said module along a spindle of said module in a first manner using a first tool to rotate said spindle in a first direction; and
executing a second changing step comprising changing a spacing between said first and second housings along said spindle in a second manner that is opposite said first manner using a second tool to rotate said spindle in a second direction that is opposite said first direction, wherein said second tool is of a different configuration than said first tool.

20. A method, as claimed in claim 19, wherein said first tool is unable to execute said second changing step.

21. An orthodontic mechanical force module, comprising:
first and second housings;
a spindle that extends within and is rotatable relative to each of said first and second housings, wherein said first housing is further threadably engaged with said spindle such that said first housing moves along a length dimension of said spindle by a rotation of said spindle to change a spacing between said first and second housings in a dimension measured along said length dimension of said spindle, wherein said spindle comprises first and second bosses that are spaced along said length dimension of said spindle and that each comprise a peripheral surface, wherein said peripheral surface of each of said first and second bosses comprises a plurality of notches disposed about a reference axis along which said spindle extends in said length dimension;
a pawl assembly that comprises a pawl, wherein said pawl is simultaneously engageable with said peripheral surface of each of said first and second bosses; and
a first guide pin that extends within each of said first and second housing, wherein said first guide pin is parallel with said spindle, and wherein said assembly is mounted on each of said spindle and said first guide pin.

22. An orthodontic mechanical force module, as claimed in claim 21, wherein:
said second housing is threadably engaged with said spindle such that said second housing moves along said length dimension of said spindle by said rotation of said spindle, wherein said first and second housings move in opposite directions along said length dimension of said spindle during said rotation of said spindle.

23. An orthodontic mechanical force module, as claimed in claim 21, wherein:

said pawl assembly comprises a concave first recess on a first side of said pawl assembly and a concave second recess on a second side of said pawl assembly opposite said first side, wherein said spindle is received within said first recess, and wherein said first guide pin is received within said second recess.

24. An orthodontic mechanical force module, as claimed in claim 21, wherein:
said pawl is resiliently biased toward said peripheral surface of each of said first and second bosses.

25. An orthodontic mechanical force module, as claimed in claim 21, wherein:
said peripheral surface of each of said first and second bosses comprises a transition section between each adjacent pair of said plurality of notches, wherein each said transition section is defined by a common radius having an origin on said reference axis along which said spindle extends in said length dimension, wherein each of said plurality of notches comprises first and second planar surfaces that intersect and that are disposed in perpendicular relation to each other, and wherein said first planar surface of each said notch extends at least generally towards said reference axis.

26. An orthodontic mechanical force module, as claimed in claim 21, wherein:
each of said plurality of notches comprises first and second planar surfaces that intersect and that are disposed in perpendicular relation to each other, and wherein said first planar surface of each said notch extends at least generally towards said reference axis.

27. An orthodontic mechanical force module, as claimed in claim 21, wherein:
said spindle further comprises first and second adjustment apertures that each extend entirely through said spindle at a location that is between said first and second bosses.

28. An orthodontic mechanical force module, as claimed in claim 27, wherein:
said first and second adjustment apertures are disposed perpendicularly to each other.

29. An orthodontic mechanical force module, as claimed in claim 27, wherein:
said first and second adjustment apertures are oriented relative to said plurality of notches such that one end of either said first or second adjustment aperture will be disposed in a first position, regardless of which of said plurality of notches on said first and second bosses is being engaged by said pawl.

30. An orthodontic mechanical force module, as claimed in claim 27, wherein:
said first and second adjustment apertures are oriented relative to said plurality of notches such that one end of either said first or second adjustment aperture will be disposed in a position for engagement by an adjustment tool to allow a full 90 degrees rotation of said spindle, regardless of which of said plurality of notches on said first and second bosses is being engaged by said pawl prior to rotating said spindle with the adjustment tool.

31. An orthodontic mechanical force module, as claimed in claim 21, wherein:
said first guide pin comprises a collar disposed between said first and second bosses, wherein movement of said first guide pin along a path that is parallel with said length dimension of said spindle is restrained by a positioning of said collar of said first guide pin between said first and second bosses of said spindle.

32. An orthodontic mechanical force module, comprising:
first and second housings;
a spindle that extends within and is rotatable relative to each of said first and second housings, wherein said first housing is further threadably engaged with said spindle such that said first housing moves along a length dimension of said spindle by a rotation of said spindle to change a spacing between said first and second housings in a dimension measured along said length dimension of said spindle, wherein said spindle comprises a plurality of notches disposed about a reference axis along which said spindle extends in said length dimension;
a pawl assembly that comprises first and second oppositely disposed sides, a concave first recess on said first side, a concave second recess on said second side, and a pawl engageable with a portion of said spindle having said plurality of notches, wherein said spindle is received within said first recess; and
a first guide pin that extends within each of said first and second housings, wherein said first guide pin is parallel with said spindle, and wherein said first guide pin is received within said second recess of said pawl assembly.

33. An orthodontic mechanical force module, as claimed in claim 32, wherein:
said second housing is thereby engaged with said spindle such that said second housing moves along said length dimension of said spindle by said rotation of said spindle, wherein said first and second housings move in opposite directions along said length dimension of said spindle during said rotation of said spindle.

34. An orthodontic mechanical module, as claimed in claim 32, wherein:
said pawl is resiliently biased toward said spindle so as to be engageable with said plurality of notches.

35. An orthodontic mechanical force module, as claimed in claim 32, wherein:
said spindle comprises first and second bosses that are spaced along said length dimension of said spindle and that each comprise a peripheral surface, wherein said plurality of notches are disposed on said peripheral surface of each of said first and second bosses.

36. An orthodontic mechanical force module, as claimed in claim 35, wherein:
said peripheral surface of each of said first and second bosses comprises a transition section between each adjacent pair of said plurality of notches, wherein each said transition section is defined by a common radius having an origin on said reference axis along which said spindle extends in said length dimension, wherein each said plurality of notches comprises first and second planar surfaces that intersect and that are disposed in perpendicular relation to each other, and wherein said first planar surface of each said notch extends at least generally towards said reference axis.

37. An orthodontic mechanical force module, as claimed in claim 35, wherein:
said spindle further comprises first and second adjustment apertures that each extend entirely through said spindle at a location that is between said first and second bosses.

38. An orthodontic mechanical force module, as claimed in claim 37, wherein:
said first and second adjustment apertures are disposed perpendicularly to each other.

39. An orthodontic mechanical force module, an claimed in claim 37, wherein:
said first and second adjustment apertures are oriented relative to said plurality of notches such that one end of either said first or second adjustment aperture will be disposed in a first position, regardless of which of said plurality of notches on said first and second bosses is being engaged by said pawl.

40. An orthodontic mechanical force module, as claimed in claim 37, wherein:
said first and second adjustment apertures are oriented relative to said plurality of notches on said first and second bosses such that one end of either said first or second adjustment aperture will be disposed in a position for engagement by an adjustment tool to allow a full 90 degrees rotation of said spindle, regardless of which of said plurality of notches is being engaged by said pawl prior to rotating said spindle with the adjustment tool.

41. An orthodontic mechanical force module, as claimed in claim 35, wherein:
each of said plurality of notches comprises first and second planar surfaces that intersect and that are disposed in perpendicular relation to each other, and wherein said first planar surface of each said notch extends at least generally towards said reference axis.

42. An orthodontic mechanical force module, as claimed in claim 35, wherein:
said first guide pin comprises a collar disposed between said first and second bosses, wherein movement of said first guide pin along a path that is parallel with said length dimension of said spindle is restrained by a positioning of said collar of said first guide pin between said first and second bosses of said spindle.

43. An orthodontic mechanical force module, comprising:
first and second housings;
a spindle that extends within and is rotatable to each of said first and second housings, wherein said first housing further threadably engaged with said spindle such that said first housing moves along a length dimension of said spindle by a rotation of said spindle to change a spacing between said first and second housings in a dimension measured along said length dimension of said spindle, wherein said spindle comprises first and second bosses that are spaced along said length dimension of said spindle and that each comprise a peripheral surface, wherein said peripheral surface of each of said first and second bosses comprises a plurality of notches disposed about a reference axis along which said spindle extends in said length dimension, wherein each of said plurality of notches comprises first and second planar surfaces that intersect and that are disposed in perpendicular relation to each other, and wherein said first planar surface of each said notch extends at least generally towards said reference axis; and
a pawl simultaneously engageable with said peripheral surface of each of said first and second bosses.

44. An orthodontic mechanical module, as claimed in claim 43, wherein:
said second housing is threadably engaged with said spindle such that said second housing moves along said length dimension of said spindle by said rotation of said spindle, wherein said first and second housings move in opposite directions along said length of said spindle during said rotation of said spindle.

45. An orthodontic mechanical module, as claimed in claim 43, further comprising:

a first guide pin that extends within each of said first and second housings, wherein said first guide pin is parallel with said spindle; and a pawl assembly that comprises said pawl, wherein said pawl assembly is mounted on each of said spindle and said first guide pin.

46. An orthodontic mechanical module, as claimed in claim 45, wherein:

said pawl assembly comprises a concave first recess on a first side of said pawl assembly and a concave second recess on a second side of said pawl assembly opposite said first side, wherein said spindle is received within said first recess, and wherein said first guide pin is received within said second recess.

47. An orthodontic mechanical force module, as claimed in claim 43, wherein:

said pawl is resiliently biased toward said peripheral surface of each of said first and second bosses.

48. An orthodontic mechanical force module, as claimed in claim 43, wherein:

said peripheral surface of each of said first and second bosses comprises a transition section between each adjacent pair of said plurality of notches, wherein each said transition section is defined by a common radius having an origin on said reference axis along which said spindle extends in said length dimension.

49. An orthodontic mechanical force module, as claimed in claim 43, wherein:

said spindle further comprises first and second adjustment apertures that each extend entirely through said spindle at a location that is between said first and second bosses.

50. An orthodontic mechanical force module, as claimed in claim 49, wherein:

said first and second adjustment apertures are disposed perpendicularly to each other.

51. An orthodontic mechanical force module, as claimed in claim 49, wherein:

said first and second adjustment apertures are oriented relative to said plurality of notches such that one end of either said first or second adjustment aperture will be disposed in a first position, regardless of which of said plurality of notches on said first and second bosses is being engaged by said pawl.

52. An orthodontic mechanical force module, as claimed in claim 49, wherein:

first and second adjustment apertures are oriented relative to said plurality of notches such that one end of either said first or second adjustment aperture will be disposed in a position for engagement by an adjustment tool to allow a full 90 degrees rotation of said spindle, regardless of which of said plurality of notches on said first and second bosses is being engaged by said pawl prior to rotating said spindle with the adjustment tool.

53. An orthodontic mechanical force module, as claimed in claim 43, further comprising:

a first guide pin that extend within each of said first and second housings, wherein said first guide pin is parallel with said spindle.

54. An orthodontic mechanical force module, as claimed in claim 53, wherein:

said first guide pin comprises a collar disposed between said first and second bosses, wherein movement of said first guide pin along a path that is parallel with said length dimension of said spindle is restrained by a positioning of said collar of said first guide pin between said first and second bosses of said spindle.

* * * * *

UNITED STATES PATENT AND TRADEMARK OFFICE
CERTIFICATE OF CORRECTION

PATENT NO. : 6,783,361 B2
DATED : August 31, 2004
INVENTOR(S) : Huge et al.

It is certified that error appears in the above-identified patent and that said Letters Patent is hereby corrected as shown below:

Column 31,
Line 54, delete "housing", and insert therefor -- housings --
Line 55, after the second occurrence of "said", insert -- pawl --.

Column 33,
Line 27, delete "thereby", and insert therefor -- threadably --.
Line 33, after "mechanical", insert -- force --.

Column 34,
Line 37, after "rotatable", insert -- relative --;
Line 39, after "housing", insert -- is --;
Line 64, after "length", insert -- dimension --;
Line 66, after "mechanical", insert -- force --.

Column 35,
Line 7, after "mechanical", insert -- force --.

Signed and Sealed this

Seventh Day of December, 2004

JON W. DUDAS
*Director of the United States Patent and Trademark Office*